(12) United States Patent
Kopelman et al.

(10) Patent No.: US 12,262,869 B2
(45) Date of Patent: Apr. 1, 2025

(54) INTRAORAL SCANNER SLEEVE AUTHENTICATION AND IDENTIFICATION

(71) Applicant: Align Technology, Inc., San Jose, CA (US)

(72) Inventors: Avi Kopelman, Palo Alto, CA (US); Michael Sabina, Campbell, CA (US); Nir Makmel, Tel Aviv (IL); Adi Levin, Nes Tziona (IL); Arad Zulti, Modi'in (IL); Arthur Hsieh, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 67 days.

(21) Appl. No.: 18/351,479

(22) Filed: Jul. 12, 2023

(65) Prior Publication Data
US 2024/0023789 A1    Jan. 25, 2024

Related U.S. Application Data

(63) Continuation of application No. 17/972,567, filed on Oct. 24, 2022, now Pat. No. 11,737,657, which is a continuation of application No. 16/841,632, filed on Apr. 6, 2020, now Pat. No. 11,478,132.
(Continued)

(51) Int. Cl.
*G16H 40/67*   (2018.01)
*A61B 1/00*    (2006.01)
(Continued)

(52) U.S. Cl.
CPC ...... *A61B 1/00142* (2013.01); *A61B 1/00103* (2013.01); *A61B 1/00172* (2013.01);
(Continued)

(58) Field of Classification Search
CPC .......... A61B 1/00142; A61B 1/00103; A61B 1/00172; A61B 1/24; A61B 5/0088; G16H 40/67; A61C 9/0053
See application file for complete search history.

(56) References Cited

U.S. PATENT DOCUMENTS

| | | | |
|---|---|---|---|
| 6,537,207 B1 | 3/2003 | Rice et al. | |
| 11,478,132 B2 | 10/2022 | Kopelman et al. | |

(Continued)

FOREIGN PATENT DOCUMENTS

| | | |
|---|---|---|
| CN | 1545681 A | 11/2004 |
| CN | 108472102 A | 8/2018 |

OTHER PUBLICATIONS

Co-pending U.S. Appl. No. 16/784,493, inventor Babayoff; Noam, filed on Feb. 7, 2020.
(Continued)

*Primary Examiner* — Jae N Noh
(74) *Attorney, Agent, or Firm* — Shay Glenn LLP

(57) ABSTRACT

Apparatuses, including sleeves, intraoral scanning systems to use these sleeves, and methods of using the sleeve, that authenticate the sleeve for use with an intraoral scanning system. Authentication may include verifying that the sleeve is new (unused) and/or verifying that the sleeve is appropriate and/or intended for use with the intraoral scanning system. Once authenticated, operation parameters of the intraoral scanning system can be automatically set based on information from a scanned identifier on the sleeve.

18 Claims, 11 Drawing Sheets

Related U.S. Application Data

(60) Provisional application No. 62/955,662, filed on Dec. 31, 2019, provisional application No. 62/830,336, filed on Apr. 5, 2019.

(51) Int. Cl.
  *A61B 1/24* (2006.01)
  *A61B 5/00* (2006.01)
  *A61C 9/00* (2006.01)

(52) U.S. Cl.
  CPC .............. *A61B 1/24* (2013.01); *A61B 5/0088* (2013.01); *A61C 9/0053* (2013.01); *G16H 40/67* (2018.01)

(56) References Cited

U.S. PATENT DOCUMENTS

| | | |
|---|---|---|
| RE49,605 E | 8/2023 | Kopelman et al. |
| 2011/0216409 A1 | 9/2011 | Stutes |
| 2014/0263674 A1 | 9/2014 | Cerveny |
| 2017/0303833 A1 | 10/2017 | Lonsinger et al. |
| 2021/0259535 A1* | 8/2021 | Shani .................. A61B 1/00096 |
| 2022/0079426 A1* | 3/2022 | Christiansen ...... A61B 1/00142 |

OTHER PUBLICATIONS

Co-pending U.S. Appl. No. 16/784,501, inventor Noam; Babayoff, filed on Feb. 7, 2020.

Co-pending U.S. Appl. No. 16/784,515, inventor Noam; Babayoff, filed on Feb. 7, 2020.

Co-pending U.S. Appl. No. 29/768,525, inventors Zakhar; Ginzburg et al., filed on Jan. 29, 2021.

Co-pending U.S. Appl. No. 29/768,563, inventors Zakhar; Ginzburg et al., filed on Jan. 29, 2021.

* cited by examiner

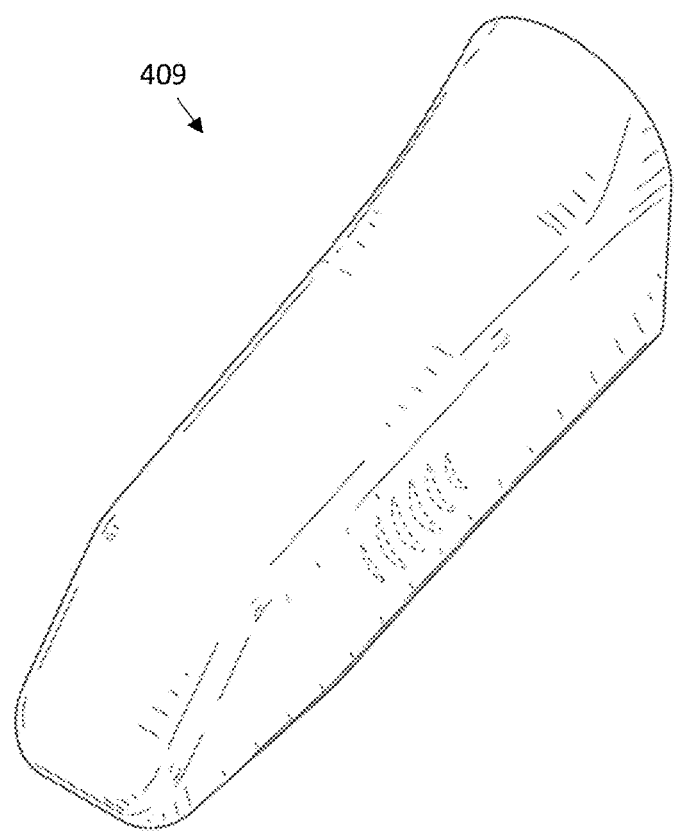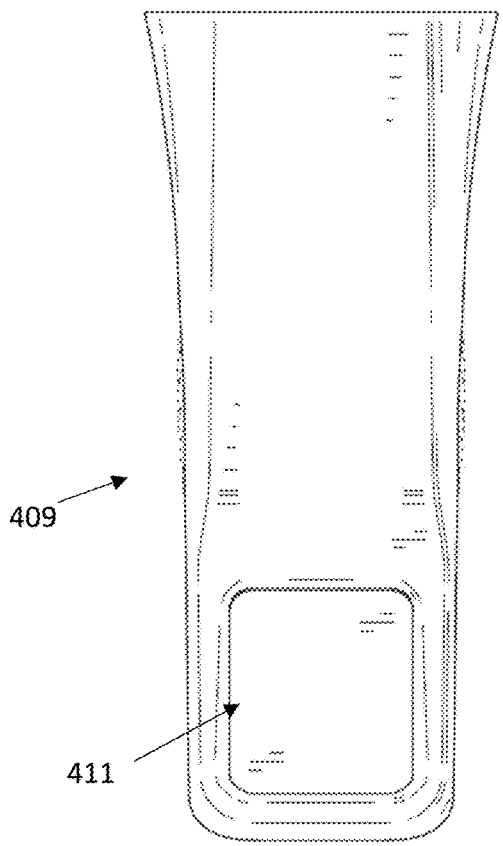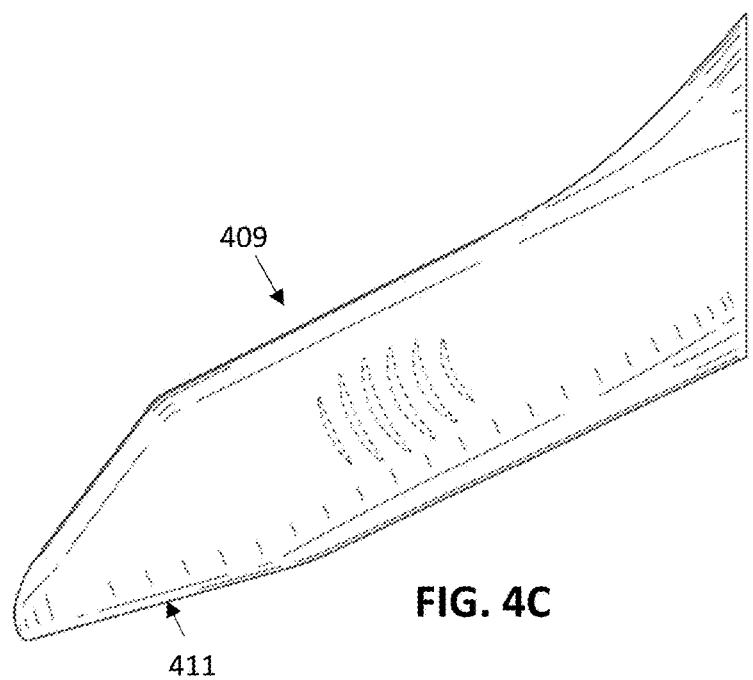
FIG. 4A
FIG. 4B
FIG. 4C

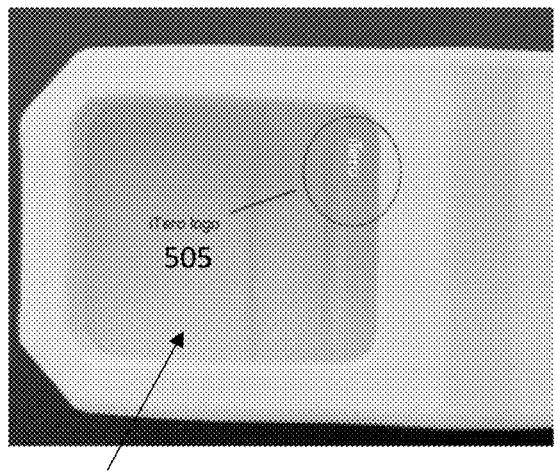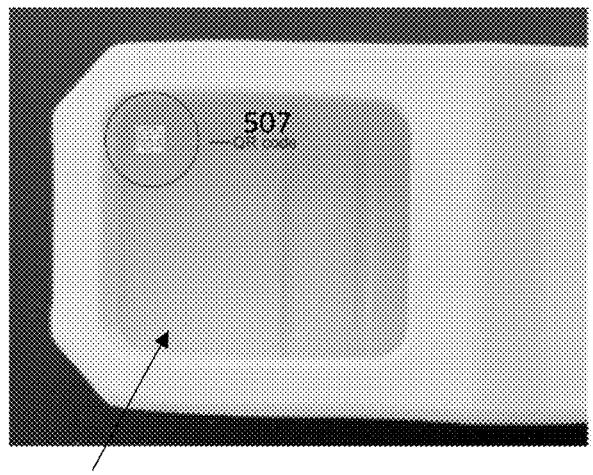
FIG. 5A  FIG. 5B
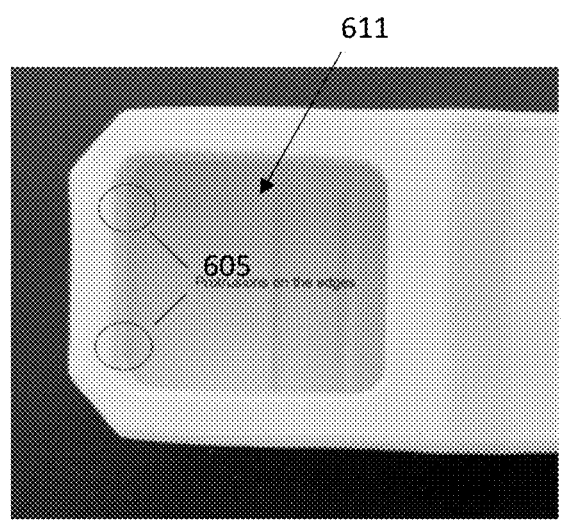
FIG. 6

INTRAORAL SCANNER SLEEVE AUTHENTICATION AND IDENTIFICATION

CLAIM OF PRIORITY

This application is a continuation of U.S. patent application Ser. No. 17/972,567, titled "INTRAORAL SCANNER SLEEVE AUTHENTICATION AND IDENTIFICATION," filed Oct. 24, 2022, now U.S. Patent Application Publication No. 2023/0040445, which is a continuation of U.S. patent application Ser. No. 16/841,632, titled "INTRAORAL SCANNER SLEEVE AUTHENTICATION AND IDENTIFICATION," filed Apr. 6, 2020, now U.S. Pat. No. 11,478,132, which claims priority to U.S. Provisional Patent Application No. 62/830,336 titled "INTRAORAL SCANNER SLEEVE AUTHENTICATION," filed on Apr. 5, 2019, and U.S. Provisional Patent Application No. 62/955,662, filed on Dec. 31, 2019, titled "INTRAORAL SCANNER SLEEVE AUTHENTICATION AND IDENTIFICATION," each of which is incorporated herein in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein may relate to protective sleeves for optical scanners, and particularly for authentication of optical sleeves for intraoral scanner that may be useful in scanning the intraoral cavity for diagnosis, treatment, longitudinal tracking, tooth measurement, and detection of dental caries and cracks.

BACKGROUND

Many dental and orthodontic procedures can benefit from accurate imaging (including, but not limited to accurate three-dimensional, 3D, imaging, 2D imaging, surface scanning, florescent scanning, etc.) to provide digital descriptions of a patient's dentation and intraoral cavity. An intraoral scanner may provide such imaging. Typically an intraoral scanner may include a hand-held sensing component for scanning within the patient's oral cavity. The hand-held component may be referred to as a wand, and may include one or more windows for transmitting and/or receiving light to form images from within the patient's oral cavity.

Because the intraoral scanners may be inserted at least partially into the patient's mouth, a protective element, referred to herein as a sleeve or as a protective sleeve, may be used with the wand. The sleeve can act as barrier between the wand and the patient to protect the patient from cross-contamination. Thus, the sleeve may be removable from the wand so that the sleeve can be replaced before using the wand with the next patient. However, it may be difficult to keep track of whether a certain sleeve is new or has already been used. In addition, the optical qualities and the shape and size of the sleeves may affect the performance of the intraoral scanner. For example, if the sleeve does not fit on the intraoral scanner properly or does not have good optical transmission properties, the intraoral scanner will not obtain a good scan of the patient's mouth, resulting in inaccurate scan results.

Described herein are methods and apparatuses, including protective sleeves, systems including protective sleeves, and methods of using them to address these problems and that may enhance the safety and functionality of intraoral scanners.

SUMMARY OF THE DISCLOSURE

Described herein are apparatuses, including sleeves, intraoral scanning systems to use these sleeves, and methods of using the sleeve, that authenticate the sleeve for use with an intraoral scanning system. Authentication may include verifying that the sleeve is new (unused) and/or verifying that the sleeve is appropriate and/or intended for use with the intraoral scanning system.

Generally described herein are sleeves for an intraoral scanner that are configured to indicate use and/or identity of the sleeve; for example descried herein are sleeves for an intraoral scanner that include one or more identifiers that may be used by the intraoral scanner to verify the identity of the sleeve and/or the use state of the sleeve (e.g., as new/original and/or unused). The sleeve may be tracked, including indicating is origin, its expiration, and any properties of the sleeve, including its compatibility with a particular intraoral scanner or class of intraoral scanners. In some variations the sleeves described herein are configured to modify the intraoral scanner, including preventing/permitting scanning, adjusting scanning parameters, etc.

For example, described herein are sleeves (e.g., protective sleeves) for use with an intraoral scanner that include: a sleeve body configured to fit onto a wand of an intraoral scanner; a window through the sleeve body formed of a transparent material, wherein the window is configured to align with a field of view of the intraoral scanner; and an identifier on the window, wherein the identifier is configured to impinge into the field of view of the intraoral scanner when the sleeve is attached to the intraoral scanner, further wherein the identifier identifies one or more of: the identity of the sleeve and the use status of the sleeve.

The identifier may be one or more of: an alphanumeric code, a logo, a symbol, a QR code, a bar code, hologram, etc. Any type of code (e.g., any type of QR code, such as model 1, model 2, MiroQR code, iQR code, etc.) may be used. The may be positioned on the window in any location, including, for example, on a position that is spaced from an edge of the window, e.g., by at least 0.1 mm (e.g., at least 0.2 m, 0.3 mm, 0.4 mm, 0.5 mm, 0.7 mm, 1 mm, 1.2 mm, 1.5 mm, etc.). Any of the identifiers described herein may comprise a use-sensitive material, such as a composition that reacts with and changes when exposed to one or more of light (e.g., a wavelength of light emitted by the scanner, such as by photo bleaching), moisture (e.g., due to the moisture of a patient's breath), carbon dioxide (e.g., changing color due to the patient's respiration, and/or exposure to air, etc.).

Any of the identifiers described herein may be printed onto the window, on either the top and/or bottom surface of the window. Also described herein are sleeves in which an identifier is formed on an inner and/or outer surface of the sleeve instead or in addition to on the sleeve window.

In some variations an identifier may be printed onto the window in a material that is visible only when illuminated by light outside of the visible spectrum (e.g., when illuminated by a florescent wavelength, by an IR/near-IR wavelength, etc.).

Alternatively or additionally, the identifier may comprise one or more of a notch or protrusion in the edge of the sleeve body extending into the window (e.g., within the field of view of the scanner).

In general, the sleeve body may configured to be worn over the wand, and/or attached to the end of the wand.

Also described herein are intraoral scanning systems. Any of these systems may be configured to include an intraoral scanner and one or more sleeves that are configured to be used with the intraoral scanner; the intraoral scanner is generally configured to detect/authenticate the sleeve to confirm that the sleeve is new (e.g., unused) and/or appropriate for use with the intraoral scanner. For example, an intraoral scanning system may include: an intraoral scanner comprising a wand having a transmission window for transmitting and/or receiving light to form images from within the patient's oral cavity and a processor, the transmission window having field of view; and a sleeve configured to be worn on the wand, the sleeve comprising a sleeve body, a sleeve window through the sleeve body, the sleeve window configured to align with the transmission window, and an identifier on the sleeve window and configured to impinge into the field of view so that the intraoral scanner may image the identifier when the sleeve is worn on the wand; wherein the intraoral scanner is configured to authenticate the sleeve by scanning the identifier.

In general, the system may be configured to limit or prevent operation of the intraoral scanner until the sleeve is authenticated (e.g., until the sleeve is authenticated as new/unused).

Any of these systems may include a database either locally and/or remotely to determine the status (e.g., used/unused, expired, region, etc.) of a sleeve indexed by an identifier associated with the sleeve. The database may be, for example, a remote database comprising a listing of identifiers including the identifier on the sleeve window, further wherein the remote database further comprises information about the sleeve associated with the identifier on the sleeve window.

Any of these systems may include a processor that is configured to authenticate the sleeve periodically during operation of the intraoral scanner (optionally, the system may be configured to prevent operation unless and until the sleeve is authenticated). The processor may include software/hardware/firmware that determined the status and/or identity of the sleeve, e.g., by analyzing the scans from the wand at a region associated with the sleeve window, or otherwise, and by identifying an identifier associated with the sleeve, applying logic to determine if the sleeve is unused/used and/or modifying operation of the scanner based on the status and/or identity of the sleeve.

The identifier may be any of the identifier described herein (e.g., one or more of: an alphanumeric code, a hologram, a logo, a symbol, a QR code, or a bar code, etc.).

Also described herein are methods of operating an intraoral scanner to verify the status of a sleeve as described herein. For example, described herein are methods of operating an intraoral scanner, the method comprising: scanning an identifier associated with a sleeve configured to be worn on a wand of an intraoral scanner; using the identifier to verify that the sleeve is unused and/or authenticated for use with the intraoral scanner; and suspending operation of the intraoral scanner until the verification confirms that the sleeve is unused and/or authenticated for use with the intraoral scanner.

For example, a method of operating an intraoral scanner may include: scanning, using a wand of the intraoral scanner, an identifier of a sleeve, wherein the identifier is located on a sleeve window and impinges into a field of view of the intraoral scanner when the sleeve is worn on a wand; verifying that the identifier is authenticated for the intraoral scanner, wherein verifying comprises confirming that the sleeve is unused prior to scanning a patient's dental arch with the intraoral scanner; and preventing the intraoral scanner from scanning the patient's dental arch until the verification confirms that the sleeve is authenticated.

Scanning may be performed when the sleeve is attached to the wand using the wand of the intraoral scanner to scan the identifier on a window through the sleeve. Alternatively, scanning may be performed prior to attaching the sleeve (e.g., by scanning the sleeve or a code associated with the sleeve with the wand and/or by manually entering a code (e.g., identifier). For example, in some variations the identifier is on a portion of a window that is within the field of view of the intraoral scanner. In some variations, scanning comprises scanning a sticker on the sleeve, wherein the sticker includes the identifier.

Scanning may comprise scanning the identifier as the sleeve is attached to the wand, and/or before the identifier is attached and/or after the sleeve is attached.

In general, using the identifier to verify that the sleeve is unused and/or authenticated for use with the scanner may comprise confirming that the sleeve is unused. Alternatively or additionally, using the identifier may comprise looking the identifier up in a database to confirm that the sleeve associated with identifier is approved for use with the intraoral scanner (e.g., has the correct optical properties, has not expired, is approved for use within a geographic region, etc.).

Generally, using the identifier may comprise looking the identifier up in a database (e.g., a remote or local database, such as an on-scanner database) to confirm that the sleeve associated with identifier is approved for use with the intraoral scanner.

In any of these methods, using the identifier may comprise examining a use-sensitive material of the identifier to confirm that the sleeve is unused (e.g., looking for exposure to light from the scanner, looking for exposure to a patient, etc., breath, etc.). Alternatively or additionally, using the identifier may comprise examining a surface of a window through the sleeve, e.g., to determine wear on the surface (scratching, condensation history, etc.).

In general, the activity of the scanner may be modified based on the status of the sleeve. For example, the use of the scanner may be suspended. In some variations suspending comprises preventing scanning of a patient's dentition with the intraoral scanner until the sleeve is confirmed as unused and/or authenticated for use with the intraoral scanner.

Any of the intraoral scanners described herein may also assist in tracking the sleeve usage. For example, any of these systems may update a database with a use status of the sleeve indexed by the identifier.

Any of the protective sleeves described herein may include a removable identifier that can be separated from the sleeve before scanning the patient's dentition. In one example, the removable identifier is on, or part of, a window cover that covers the optical window of the sleeve prior to use. The window cover may be a protective cover that protects the window, for example, during storage or handling of the sleeve.

Any of the intraoral scanners described herein may also be configured to operate under one or more use modes. The identifier of a sleeve may include information associated with one or more particular use modes for the scanner to operate when using the particular sleeve. The use mode may be based on physical characteristics of the sleeve and/or based on desired permissions of the user using the sleeve. The use mode of an intraoral scanner may be automatically set when the scanner scans the identifier.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A-4C illustrate perspective bottom and side views, respectively of a sleeve (e.g., protective sleeve) for an intraoral scanner. Any of these sleeves may include an identifier and/or a use-indicating material as described herein.

FIGS. 5A-5B show examples of sleeves having an identifier (shown as a symbol in FIG. 5A and a QR code in FIG. 5B) on a sleeve window (offset from the edge of the sleeve window and within a field of view of an intraoral scanner when the sleeve is applied to the intraoral scanner wand).

FIG. 6 is another example of a sleeve including an identifier that may be detected by an intraoral scanner; the identifier in this example is configured as protrusions on the edge of the sleeve.

DETAILED DESCRIPTION

Figure 1:
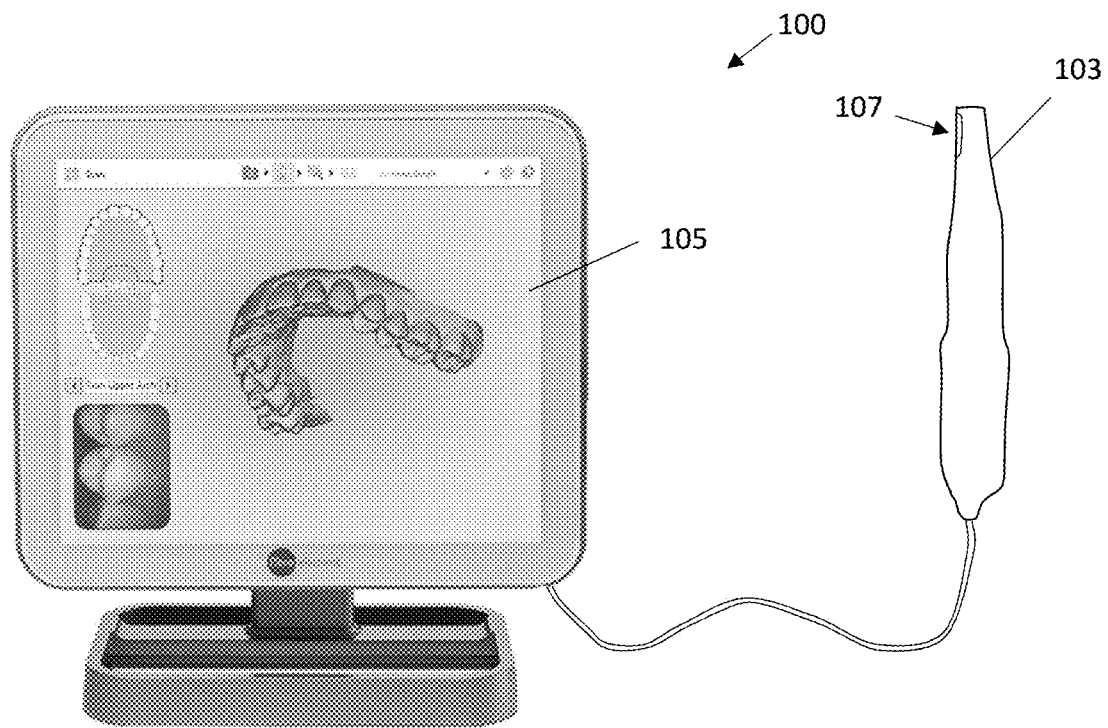
FIG. 1 is an example of one variations of an intraoral scanner as described herein.

In general, described herein are protective sleeves for use with intraoral scanners. The protective sleeves may include a body portion, which may be configured to attach to a hand-held wand portion of an intraoral scanner, and a window portion through which the intraoral scanner may transmit light and/or receive images. The window portion may be covered or uncovered. In particular, described herein are protective sleeves configured to allow authentication as well as systems including such sleeves that are configured to authenticate them and methods of using them.

As used herein the term authentication may include determining, by the intraoral scanner, the identity and/or characteristics of a sleeve to be coupled with the intraoral scanner. In some variations authentication refers to proving the identity of a sleeve or sleeves. In some variations authentication include verifying that the sleeve is a valid, approved and/or compatible sleeve for use with the intraoral scanner. In some variations, authentication include identifying if the sleeve has been previously used (by the particular intraoral scanner and/or another intraoral scanner). In some variations authentication includes activating and/or modifying the operation of the intraoral scanner in response to the sleeve.

A protective sleeve may be configured as a rigid, semi-rigid or compliant body that may mate with a hand-held wand portion of an intraoral scanner. The body may be configured to extend over the wand; the protective sleeve may form a barrier against the transmission of contamination such as bacteria, viruses, and like. The body may be configured to act specifically as a barrier to saliva, mucus and other biological fluids. In some variations the protective sleeve, including the body of the protective sleeve, may be formed at least in part from a polymeric material, such as a silicone, latex or other polymer. The body of the sleeve may extend over the wand and/or all or some of a cord or cable. For example, the sleeve, including the window and body of the sleeve (also including any extension of the sleeve) may be formed of a flexible barrier material (e.g., a plastic or other polymeric material) that may provide a fluid and/or pathogen barrier.

The protective sleeve may include a window portion that is configured to align with a corresponding window on the wand to transmit light and/or other information for forming images of the patient's dental cavity. The window region may be sized and/or shaped to match or refine the imaging window of the wand. As will be described in some variations, below, the sleeve window may be sized and/or shaped so that at least a portion of the sleeve window projects or extends at least partially into the field of view of the imaging window of the wand, in order to aid in authentication. The sleeve window may be formed of a transparent material, and in particular may be formed of a material that is transparent to the one or more wavelength(s) used by the intraoral scanner for imaging the patient's dentition. For example, the sleeve window may be formed of an optically clear material, or a material that is transparent in the optical wavelengths and/or the fluorescent wavelength(s) being used and/or the near-infrared wavelengths. The sleeve window may be formed of a material that is rigid or semi-rigid and may be a polymeric material, e.g., polycarbonate, polymethyl methacrylate (PMMA), polyethylene terephthalate (PET), amorphous copolyesters, polyvinyl chloride (PVC), liquid silicone rubber (LSR), cyclic olefin copolymers, polyethylene (PE), ionomer resin, transparent polypropylene (PP), fluorinated ethylene propylene (FEP), methyl methacrylate-acrylonitrile-butadiene-styrene (MABS, e.g., transparent ABS), polystyrene (general purpose—GPPS), styrene methyl methacrylate (SMMA), etc. One or more material (including layers of materials) may be used. The sleeve window may be sealed to the body portion to perfect the barrier against biological contamination. In some variations, all or a portion of the sleeve may also be formed of the same material as the window. In some variations the sleeve may be formed of a material that is different from the window.

In general, the protective sleeve may mate with and engage the intraoral scanner. For example, the protective sleeve may be configured to cover a hand-held wand of an intraoral scanner. In some variations the protective sleeve extends over the end of the hand-held wand so that the window of the protective sleeve aligns with the imaging window of the wand. The body of the protective sleeve may extend over the hand-held wand and in some variations down the body of the wand some distance (e.g., 6 inches or more, 8 inches or more, 12 inches or more, 16 inches or more, 2 feet or more, 3 feet or more, 4 feet or more, 5 feet or more, etc.).

In some variations the protective sleeve may also be textured for gripping (e.g. by a user's hand) securely when operating the intraoral scanner. The protective sleeve may also include one or more ridges, bumps, channels, textures, etc., to assist in gripping.

A protective sleeve comprises a housing configured to fit over a portion of an intraoral scanning device and protect the intraoral scanning device from an external environment. The intraoral scanning device comprises a first aperture for transmission of optical signals, the housing defines a second aperture for transmission of the optical signals, and the second aperture is aligned with the first aperture when the housing is fit over the portion. The protective housing comprises one or more supports attached to the housing and a transparent element secured by the one or more supports and aligned with the second aperture. The transparent element is further aligned with a defogging element of the intraoral scanning device when the housing is fit over the portion, and an external surface of the transparent element is to receive heat generated by the defogging element to prevent fogging of the transparent element.

The protective sleeves described herein may include additional materials and components, including lighting (e.g., one or more LEDs), sensors, circuitry, or the like, which may be embedded and/or held within the protective sleeves.

Any of the protective sleeves and/or intraoral scanners described herein are configured to permit authentication of a particular sleeve. As mentioned, authentication may refer to authentication of the identity or category of the sleeve as preapproved for use with a particular intraoral scanner, which may confirm that the sleeve is appropriate for use with that intraoral scanner as well as uniquely and/or categorically identifying the protective sleeve for tracking, monitoring, and adjusting scanning parameters (e.g., imaging parameters, cost parameters, etc.). In some variations authentication may include identifying and/or confirming the identity of a particular protective sleeve, class of sleeve, type of sleeve, lot and/or batch of sleeves, etc. In some variations, authentication may include uniquely identifying a particular protective sleeve. The identity of the particular sleeve may be used to track the protective sleeve, including monitoring the use of that sleeve for a particular patient. Alternatively or additionally, authentication may include confirming that a sleeve is a member of a particular class or lot of sleeves; the class or lot of sleeves may be used to confirm that the protective sleeve(s) is being used with the correct intraoral scanner, that there are not issues (e.g., recalls) on that class or lot, that the settings for the intraoral scanner are correct for use with the sleeve, etc.

Authenticating protective sleeves to be used by an intraoral scanner as described herein may provide a number of significant advantages, including protecting the patient, user (e.g., doctor, dentist, orthodontist, dental technician, etc.) and/or the intraoral scanner. For example, in some variations authentication of a protective sleeve for an intraoral scanner may be done to ensure that a particular sleeve is used with a single patient, in order to prevent cross-contamination between patients. For example, the sleeves and methods of authenticating them described herein may ensure that only original (e.g., new, unused, and/or in some variations sterilized) sleeves will be used with the intraoral scanner. When authentication includes determining a unique identifier of the protective sleeve, the intraoral scanning system may read or receive (or determine) the unique identifier and may modify the operation of the intraoral scanner to limit the operation of the intraoral scanner so that the particular, authenticated and identified protective sleeve may only be used with a single patient.

In some variations the sleeve may include one or more indicators that may indicate that the sleeve has been used already and/or that the sleeve has been cleaned, such as sanitized, washed, autoclaved, sterilized, etc. For example the one or more indicators may indicate when a sleeve has been exposed to a high temperature for sufficient time to sterilize the sleeve. In some variations this may be detected by an optical change (e.g., a mark or marker that reacts to the high temperature and/or humidity, etc. characteristic of sterilization). For example the one or more markers may be thermal exposure indicators, fluid/water exposure indicators, radiation indicators, etc.

Thus, authentication may include authenticating that the sleeve is unused and/or that the sleeve has been used and sterilized. In some variations sleeves may be designated as single-use, as described herein. In some variations, the sleeves may be configured to be used more than once (e.g., twice, three time, four times, etc.). For example, a two-use sleeve may be used once (in some variations its use may be recorded on the apparatus when initially authenticating it prior to or as it is applied for use. Thereafter the sleeve may be cleaned and/or sterilized and used for a second time; the sterilization may mark or trigger marking on the sleeve being sterilized, as mentioned above.

In some variations the sleeve may be authenticated with a unique code and this code may be associated with a particular user, e.g., within a database of or accessibly by the intraoral scanner. Thereafter the sleeve may only be used with the user for which it is associated.

In some variations, the use of a sleeve as described herein may ensure that the scan quality of the intraoral scanner remains high, since the identified protective sleeve may be matched to the operation of the intraoral scanner. This may also help ensure clinical safety, preventing contamination between patients. In some variations, the methods and apparatuses described herein may adjust the behavior of the intraoral scanner. In addition to turning on/off the scanner, e.g., only operating the intraoral scanner when an approved, and/or unused sleeve has been authentication on the wand, the systems and methods described herein may also or alternatively modify the behavior of the scanner by adjusting the scanning parameters to accommodate characteristics (e.g., optical properties) associated with the sleeve and/or the intraoral scanner.

As will be described in greater detail below, the systems and methods described herein may allow local and/or remote authentication of the protective sleeve. For example, in some variations the identity of a particular sleeve may be determined using a local technique (e.g., without requiring access to a remote server, database or the like).

Authentication of sleeves may allow an intraoral system to determine the origin of the sleeve, including matching and enforcing a geographic region or zone in which the sleeve is permitted to be used. For example, it is possible that regulatory rules of different countries, regions or states may require limiting the operation of a sleeve to a single patient and/or a single session before a new sleeve must be applied. By authenticating and tracking a protective sleeve, a system may confirm that that sleeve is appropriate for use in the region in which the intraoral scanner is being operated. Geographic region may be determined by checking, for example, the local address and/or an internet IP address associated with the intraoral scanner or user of the scanner against permissions (and/or zone, region, etc. identifier) associated with the identifier of the protective sleeve.

As mentioned, any of the methods and apparatuses described herein may be configured so that authentication enables enforcement of a single use (e.g., single continuous use) of a sleeve with a scanner, and/or use limited to a single patient. Alternatively, the methods and apparatuses described herein may be configured to allow multiple uses. In some variations the methods and apparatuses may be configured to detect cleaning and/or sterilization of the sleeve and may allow additional use(s) following cleaning and/or sterilization. The apparatuses (e.g., systems, devices, etc.) described herein, including the intraoral scanners may be configured to include a particular case or patient associated with a case as a scan is recorded. Interrupting the scan by more than a predetermined period of time (e.g., one hour, two hours, four hours, six hours, 12 hours, 1 day, etc.), starting a new case and/or ending or closing a patient session, may result in the system locking the use of the scanner for the current protective sleeve based on the sleeve identity. Thus, the sleeve may be identified going forward as "used". In some variations, a used/unused tag may be associated with each uniquely identified sleeve. Additional identifiers, including an identifier associating the particular sleeve with a particular patient, a particular intraoral scanner, a particular geographic location, a particular user, etc., may also or alternatively be used. Thus the authentication may include associating one or more additional identifiers (use, patient, etc.) with the sleeve identifier in a local or remove (e.g., cloud-based) database or data store.

In some variations a count may be associated with each sleeve as an additional identifier. For example, the count may indicate the number of uses (e.g., a single use or uses), which may be used in some apparatuses to provide or limit the number of uses that a sleeve may be used. For example, the systems described herein may be configured to identify a particular sleeve and permit that sleeve to be used on an intraoral scanner a pre-defined number of times.

In some variations a date and/or time, such as an expiration date, may be associated, including as an additional identifier or as part of the unique identifier of the sleeve. In general, the identifier may be an alphanumeric code that uniquely identifies the sleeve. Part of the alphanumeric code identifier may be based on the date and/or location in which the sleeve was manufactured, it's lot number, etc. An expiration date may be calculated from this date information. Alternatively or additionally, an expiration date and/or manufacturing date may be associated as an additional identifier for the sleeve.

Authentication and/or identification of a sleeve may be used to mark or modify a case and/or scans taken for a case. For example, the sleeves described herein may be used for any scan type, and the identity of the sleeve used to take the scan(s) (e.g., sleeve identifier and/or any additional identifiers may be associated with the scan(s)) may be included, e.g., as metadata, with the case information, and/or all or some of the scans taken with the case. Associating a scan with a particular sleeve may allow tracking of errors associated with the sleeves, and/or may be used for commercial effects, including associating pricing of sleeves, and/or scans.

FIG. 1 illustrates one example of an intraoral scanner as described herein. One example of an intraoral scanner 100 is the iTero® intraoral digital scanner manufactured by Align Technology, Inc. In general, an intraoral scanner may include a hand-held wand 103, which may include an optical system (including projection/imaging optics) comprising one or more lenses and having an optical axis. The apparatus may also include illumination optics. The apparatus can comprise an axial scanner (e.g., a depth scanning module) that is configured to be move the projection/imaging optics system along the optical axis. The apparatus may include a beam splitter configured to transmit light from the light source (after passing through the pattern) to the object and reflect light returning from the object onto an imaging sensor. Thus, the apparatus may include an image sensor configured to receive light returning from the object (via the projection/imaging optics) through the beam splitter. The apparatus can be configured for 3D scanning to at least a portion of the object, for example, intraoral dental 3D scanning for all derivatives of dental restorative and orthodontics indications. The apparatuses for confocal scanning disclosed here can include a confocal illuminator. The optical system may include a projection/imaging system or subsystem including projection optics and imaging optics. For example, the projection optics and the imaging optics can be configured to share the same optical elements (lenses) and the same optical path. The apparatus can comprise the depth scanning module, which comprise a compact linear actuator, for example, a voice coil motor (VCM). The scanner can comprise a front tip, which can include a 45 degree (e.g., back-heated defogging) fold mirror.

The scanner may include one or more processors and may include on ore more illumination sources (LEDs, lasers, etc.). In FIG. 1, the hand-held wand 103 also include a window 107 providing optical access into the scanner. The window may include an optically transparent cover. The scanner may be wireless or wired to additional components of the system, including one or more additional processors. The scanner may generally illuminate and/or image in the visible spectrum, in the infrared or near-infrared spectrum, in the florescence spectrum, etc. A display 105 may also be included as part of the system. The intraoral scanner shown in FIG. 1 may be used with one or more sleeves, as shown in FIGS. 2 and 3.

Figure 2:
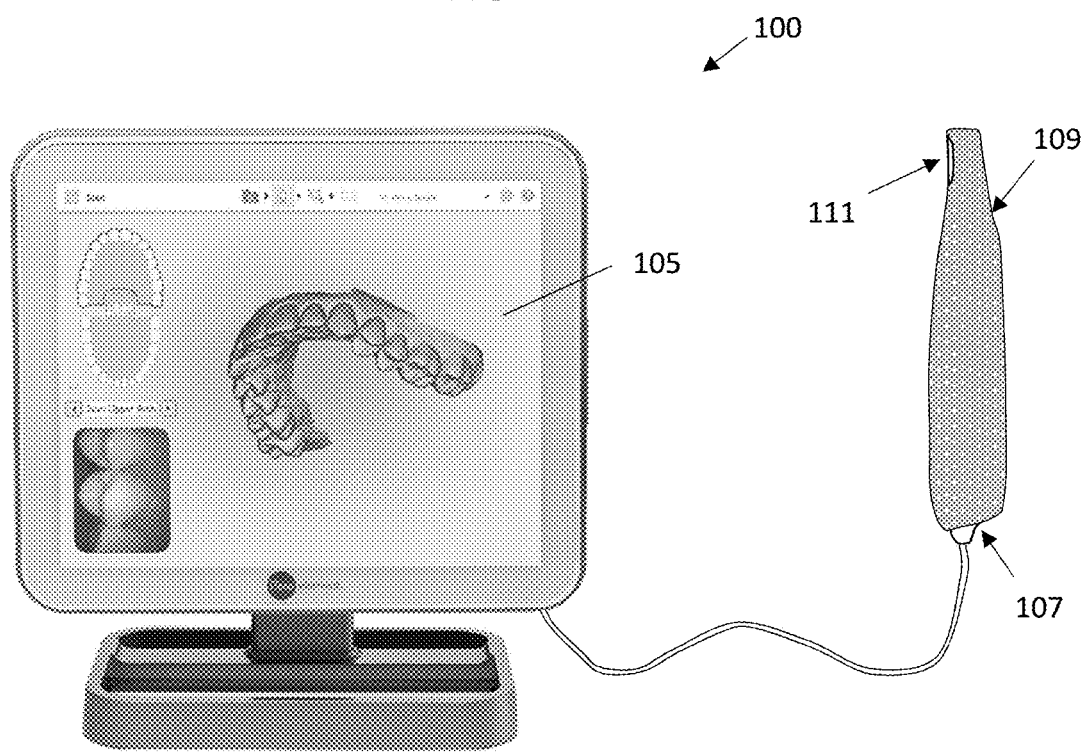
FIG. 2 illustrates the use of a protective sleeve with the example of the intraoral scanner as described herein. The sleeve may include an identifier that is automatically or manually detected by the intraoral scanner for determining the use parameter(s) of the sleeve, including if the sleeve is used or unused and/or is appropriate for use with the intraoral scanner.
Figure 3:
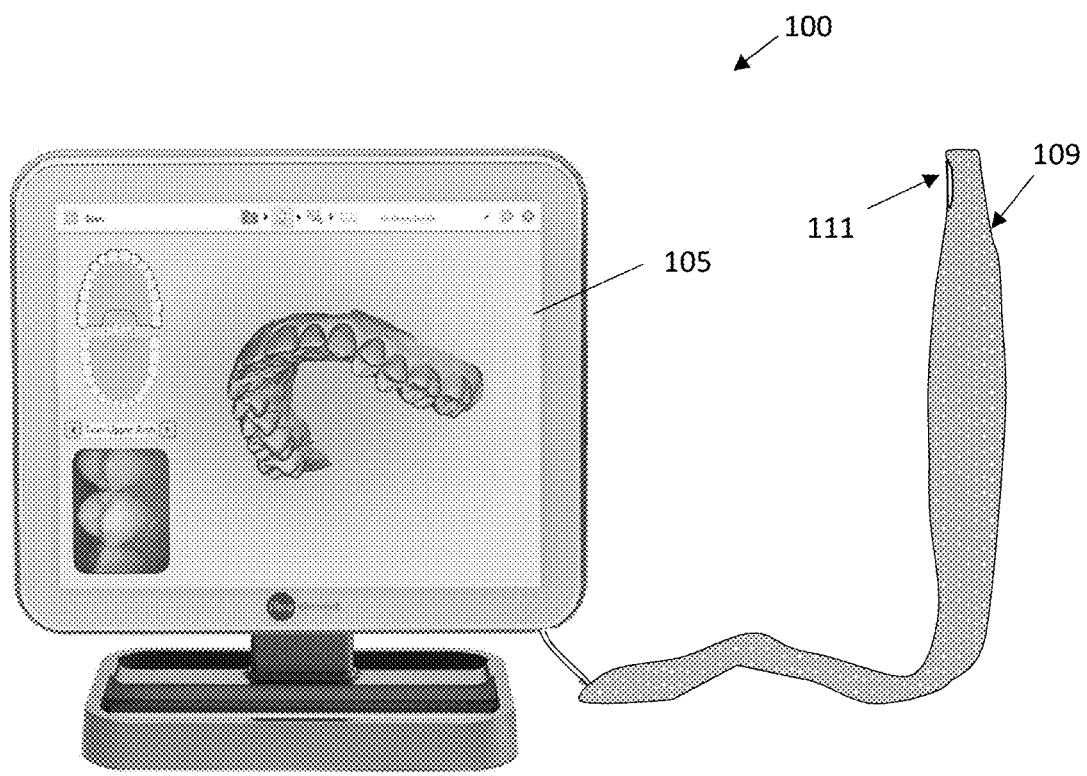
FIG. 3 illustrates another example of a system including a protective sleeve and an intraoral scanner.

In FIG. 2, the intraoral scanner 100 includes a protective sleeve 109 that is placed over the hand-held wand 103, so that a sleeve window 111 is aligned with the window in the scanner 107 (not visible in FIG. 2). FIG. 3 shows an alternative variation in which the sleeve 109 is longer, extending over the wand and connecting cable.

FIGS. 4A-4C illustrate one example of a protective sleeve 409 which may be authenticated as described herein, including one or more authentication features. In FIG. 4A, the sleeve 409 is formed of a semi-rigid material, and is configured to be placed over a hand-held wand of an intraoral scanner, as shown in FIG. 2. FIG. 4B shows the sleeve of FIG. 4A from a bottom view, showing the window 411 through which optical transmission may occur. Finally, FIG. 4C shows a side perspective view of the sleeve; the window 411 is on the bottom surface.

Any of the apparatuses and methods for authentication and/or tracking of sleeves described herein may include authentication and/or identification based impinging the field of view of the apparatus with an identification indicator. In some variations, the marking or indication may be included in the window of the sleeve.

Window-Based Authentication

Thus, in any of the apparatuses or methods described herein, an identifier (which may include a symbol, letter, number, pattern, color, or any combination of these) that may uniquely or categorically identify the sleeve for detection by the scanner, and in particular for direct detection by the hand-held wand and imaging portion of the scanner. Despite impinging in the field of view, the systems, including the intraoral scanning systems, described herein may automatically detect and verify (e.g., authenticate) the identifier and scan the patient. For example, in some variations the identifier may be an indicator in the window of the sleeve. The vision system of the scanner itself may then see the indicator and determine if the sleeve is authenticated for use. The scanner may be configured to ignore the indicator for the purpose of scanning. The verification can either happen at the beginning (e.g., at the start of scanning) or multiple times during the scanning procedure (e.g., periodically at regular intervals, such as every few seconds, every minute, every 2 minutes, every 3 minutes, etc., at random intervals, etc.).

FIGS. 5A and 5B illustrate examples of indicators marked onto the window of the sleeve. In FIG. 5A the identifier is a graphical and textual marker 505 resembling a logo that is positioned in a predefined region of the window 511 of the sleeve. In this example, the indicator is in the bottom right portion of the window of the sleeve and is configured to impinge into the scanning field of view of the intraoral scanner when the sleeve is placed over the wand, e.g., so that the wand imaging window is aligned with the window in the sleeve.

Figure 9:
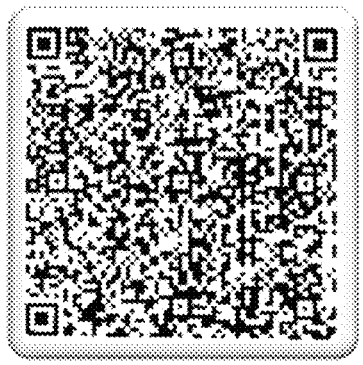
FIG. 9 illustrates an example of a QR code.

FIG. 5B is another example of an identifier 507, shown here configured as a QR code that includes information that may be uniquely linked to the protector sleeve. In FIG. 5B the identifier (e.g., QR marker or any or marker that includes identifying information) may be positioned on a portion of the sleeve that impinges into the field of view and may be detected by the intraoral scanner. FIG. 9 shows a close-up view of an example QR code.

In general, the location and/or orientation of the identifier may be used for authentication, and may be detected and/or verified by the intraoral scanner. As mentioned, the intraoral scanner may detect the identifier in the field of view of the scanner and may be configured to image the teeth through or around the marker, without significantly impacting the quality of scans.

As mentioned, any appropriate identifier may be used. The identifier may be matched to the scanning functionality of the intraoral scanner. Specifically, the identifier may be in color (including in non-visible color, such as IR/near-IR, florescent, etc.) and may be detected only upon illumination by the appropriate wavelength(s) of light and detection by the intraoral scanner. Different regions of the identifier may be in different colors, fonts, etc., which may provide additional information for authentication. In general, the colors(s) and/or the sizes of the identifier may indicate the version, location, permissions and etc. associated with the sleeve. In some variations the identifier may be in a different color for portions of the identifier, and/or different fonts may be used.

The identifier may include parts that are only visible when illuminated by a specific wavelength or wavelengths of light emitted by the sensor through the window in the wand. For example, as mentioned above, the identifier may be marked using a material that is only visible (or fully visible) when illuminated using a specific wavelength light e.g. near-IR light (NIRI). Alternatively or additionally, the identifier may be formed at least in part of a material that is reflective for a specific wavelength.

Another form of directly scanned identification may include one or more identifier markings on either the sleeve and/or on the packaging and/or on packaging insert(s) accompanying the sleeve. For example, in some variations the sleeve may include a making on the inside or outside of the sleeve that may be imaged before or during attachment of the sleeve to the wand.

In some variations, the sleeve may include an identifier that is present in the inside of the sleeve that may be imaged by the intraoral scanner when attaching the protective sleeve to the wand. The protective sleeve may be attached to the intraoral scanner with the intraoral scanner 'on' and scanning; scanning may detect the identifier in the intraoral scanner. The identifier may be formed, printed or otherwise attached to an inner surface of the sleeve, including but not limited to the window of the sleeve and/or a region that is proximal to the window within the sleeve, so that it may be viewed by the intraoral scanner when attaching. In some variations a sticker or other member including the identifier may be attached to the inside of the intraoral sleeve. Alternatively in some variations the identifier may be pressed or formed into the sleeve, including into the body portion of the intraoral scanner.

An intraoral scanner may be configured to include an attachment mode for attaching the protective sleeve, verifying both that the sleeve is attached and verifying that the sleeve is authentic (e.g., new and/or approved for use with the intraoral scanner, etc.).

Any of the sleeves described herein may include an identifier one an outside surface of the intraoral scanner that may be scanned by the intraoral scanner. For example, when turning the intraoral scanner on, the system may enter into a sleeve authentication mode, in which the scanner waits to receive (using the wand itself) an image or scan of the indemnifier before proceeding. Thus, if the identifier is attached, formed or otherwise an outer surface of the sleeve (including, but not limited to, the window of the sleeve), then scanner may, within a predefined time for activating the intraoral scanner, detect when the identifier and confirm authenticity and/or appropriateness of using that sleeve with the scanner. In some variations this may then allow the scanner to proceed to preparing to scan the subject/patient. As mentioned the identifier may be printed, formed or attached to the outside of intraoral sleeve and may be directly scanned by the intraoral scanner wand either before, during, or after attaching the sleeve.

In some variations the identifier is packaged with the sleeve and may be scanned by the wand. For example, a paper, sticker, etc. may be marked with the identifier for the sleeve and may be directly scanned by the intraoral scanner.

Any of the methods and apparatuses described herein may alternatively or additionally use an identifier that is manually entered by the user into the intraoral scanner to verify the sleeve, track use of the sleeve and/or adjust the operation of the intraoral scanner using the sleeve. For example, an identifier that includes a symbolic or an alphanumeric code may be entered into the scanner manually. The scanner may then verify the identity and/or restrict or allow scanning using the sleeve.

In some variations, the identifier, including identifiers on all or a portion of the window may be used both as an identifier and as an optical target for adjusting, setting and/or calibrating one or more parameters of the intraoral scanner. For example, when the identifier is on the window, the identifier may be used to calibrate the intraoral scanner wand for more accurate scanning of the intraoral cavity (e.g., teeth, gingiva, palate, etc.).

Types of Identifiers

In general, any appropriate identifier may be used. For example, when alphanumeric identifiers are used, the alphanumeric identifier may be printed in a specific color, font, etc. that also provides additional information and/or verification.

Any of the identifiers described herein may include self-referencing in the encoded information, in which the as encoded information is keyed so that an analysis of the encoded key may provide an initial verification that the identifier is valid. This may be achieve by enclosing the identifier using a technique similar to an error correcting code, in which the intraoral scanner may locally (e.g., without requiring access to a remote database) confirm that the identifier is likely correct; more detailed information on the identity and actions taken with the sleeve may later be remotely retrieved and/or stored.

For example, the identifier may be configured so that it includes portions (e.g., blocks) that are, e.g., traditionally partitioned to include regions that code for checks to the information within the identifier (e.g., block codes and/or convolutional codes, and/or turbo codes). These codes may allow for encoding and decoding algorithms that may be used to determine the likely veracity of the identifier read by the apparatus. For example, the identifier may include a forward error correction region; a portion of the identifier may be used by the local intraoral scanner (after being directly detected by the scanner and/or entered by a user into the scanner), to determine the likelihood that the rest of the identifier is accurate. A Hamming code is one example of a linear binary code which may include additional characters that may be used to verify the accuracy of the other digits. Thus, even if the intraoral scanner is not connected to a remote server or is unable to connect to a remote server reliably, it may at least initially verify that an identifier corresponds to a legitimate protective sleeve. The identifier may be later confirmed as legitimate by accessing a remote server, remote database, etc.

In general, scans taken with an invalid (unverified or authenticated) protective sleeve may be later adjusted (e.g., marked as invalid, etc.). In variations in which the scan is tentatively (e.g., locally) identified as legitimate, but which later authentication indicates is not authenticated may be adjusted, marked, deleted, or otherwise indicated as coming from an invalid protective sleeve. Alternatively in some variations a failure of authentication does not stop the scanning, but merely results in marking of the scan(s) that it was taken with an invalid protection sleeve.

Use Verification

In addition or as an alternative to the use of identifiers described herein, any of these methods and apparatuses (e.g., systems, including intraoral scanners, sleeves, etc.) may be configured to detect the presence of a sleeve, as well as the prior use of a sleeve even with the use of an identifier. An intraoral scanner, including, but not limited to confocal intraoral scanners, may detect the presence of a sleeve window by detecting the presence of even a visually transparent window covering the imaging window of the wand, even in the absence of an explicit identifier. The scanner may be configured to scan the depth at which the sleeve window will be present when a sleeve is attached to the scanner and may detect reflections, scratches, and surface imperfections from the sleeve window. Such reflections and imperfections are typically present even when a new and 'clean' sleeve is attached to the wand.

Thus, any of the systems described herein may automatically detect the presence of a sleeve when worn on the wand by detecting and/or characterizing the sleeve window based on the reflections/imperfections arising due to the sleeve window. In some variations the characterization of the sleeve window when the system is initially activated, e.g., to start a patient scanning system, may be examined to determine that the sleeve window is characteristic of a new sleeve and/or may have characteristics corresponding to an authenticated sleeve. For example, authenticated sleeves may be those that are sufficiently clean, smooth, non-reflective, etc. over one or more wavelengths to be used by the scanner. The intraoral scanner may therefore be configured to initially scan the sleeve window itself (based on the expected location/depth of the sleeve window when attached and/or based on a detection routine that identifies the depth of the sleeve window). The entire sleeve window may be examined and compared to expected values to confirm that a sleeve is attached and/or that the sleeve window is characterized within approved parameters (e.g., for new, authentic sleeves). For example, the analysis of the sleeve window may generate a value or set of values based on the examination (indicating reflectance, surface flaws, smoothness, scratches, surface deposits, etc.); this value or set of values may be compared to expected values for an authenticated and/or 'new' sleeve.

For example, some systems may be configured to detect the use of a used sleeve based on imaging and analysis of the sleeve window, including the outer surface of the sleeve window and/or a comparison between the inner surface of the sleeve window and the outer surface of the sleeve window. In some variations the outer surface of the sleeve window may accumulate material (saliva, condensations due to breath, etc.) and/or use markings (scratches, etc.) over time with use. Thus, by examining the sleeve window (or in some variations a comparison between the outer surface of the sleeve window and the inner surface of the sleeve window), the system may determine or track use, and may identify when a used sleeve is attached to a wand; when a used sleeve is attached the system may require removal and attachment of a new sleeve. Alternatively or additional the system may request or determined a new sleeve after a particular amount of use. Preventing the use of 'used' sleeves in this manner may be done instead of, or in addition to, detecting an identifier as described above.

In any of the sleeves described herein, the sleeve (e.g., sleeve window) may be coated, marked, formed from, or otherwise include a material that changes with use in a manner that may be detected by the intraoral scanner (use-sensitive materials). For example, in some variations the method may include a marking and/or coating, e.g., on an outer surface of the sleeve window, with a material that reacts to exposure to air and/or breath exposes. Such materials may be include colorimetric materials that change color based on carbon dioxide and/or pH; for example, a material that reacts with carbon dioxide from breach (such as bromothymol blue, calcium hydroxide, etc.) may change pH and or color; a pH color indicator may also be used. This change in color may be dependent upon the amount of exposure to a patient's breath may therefore be used to detect use of the sleeve by the intraoral scanner. The system may be configured to require a new sleeve at the start of a patient scanning session. In some variations, the marking material (e.g., color-changing indicator) may further be arranged into an identifier (e.g., code, pattern, logo, etc.) that may be detected for verification even before use of the sleeve, as described above. As mentioned, any combination of identifier categories may be used, including, for example, a combination of a logo and a code (e.g., a logo with a code, such as a QR code, embedded in it, etc.).

Other use-sensitive materials or markings may be included. For example, in some variations the sleeve window may include a material that changes with exposure to light, including in particular the lights used for scanning. In some variations the use-sensitive marking may form or be part of an identifier. Thus, use of the sleeve may modify the use-sensitive marking/identifier (e.g., marking with a light-sensitive material) intentionally or with normal use, indicating that is has been used. For example, the system may be configure to "mark" a sleeve by directing light to the use-sensitive marking. Examples of use-sensitive markings including materials that photobleach with exposure to one or more wavelengths of light (e.g., florescent light, UV light, infrared/near-IR light, visible light, etc.). The use-sensitive marking may be present within a portion of the field of view of the sensor when the sleeve is attached, or it may extend over the entire field of view. In some variations, the system may verify the newness of the sleeve by detecting the use-sensitive marking and may actively or passively modify the use-sensitive marking to indicate that the sleeve has been used.

Sleeve Structure

Any of the methods and apparatuses described herein may also be configured to include a sleeve in which the identifier corresponds to one or more physical features, such as notches, protrusions (e.g., bumps, projections, etc.) on the sleeve, including in the sleeve window, such as the periphery of the sleeve window, that may be within the field of view of the intraoral scanner when the sleeve is attached, and may therefore be detected by the intraoral scanner. For example, one or more physical features may be formed or added to the sleeve itself in the areas exposed to the camera, as shown in FIG. 6. In this example, the features are miniature protrusions or bumps 605 on the edges of the opening of the sleeve window 611. Information about the sleeve may be encoded in the number, size and/or positions of the features (e.g., notches, bumps, protrusions, etc.).

In any of the methods and apparatuses described herein, the apparatus may automatically identify if the sleeve is new or used. In some variations, as described above, this may be determined by comparing the sleeve identity (e.g., based on an identifier) and comparing it to a local and/or remote database including information about the identified sleeve. Alternatively or additionally, the sleeve may include a use-sensitive materials and/or markings, as described above. Thus, any of the apparatuses, including intraoral scanning systems and/or sleeves, described herein may be configured to automatically identify when a sleeve is new or has been previously used. In some variations, this may be part of the authentication of the sleeve and may modify the operation of the use of intraoral scanner, which may require a new sleeve with each patient (e.g., at the start of the patient scanning session). In some variations this may include authentication of a sleeve based on the sleeve identifier (e.g., number, symbol, alphanumeric, QR code, bar code, etc.) to confirm that this sleeve is new and unused based on a remote central server/database and/or a local server/database. Any of these systems may communicate use and other information about an identified sleeve to the local and/or remote sleeve database (e.g., a server maintaining the sleeve database).

As mentioned above, any of these systems may be configured to use the imaging properties of the intraoral sensor (e.g., wand) to confirm the authenticity, newness and/or validity of a sleeve. In particular, any of these system may be configured to use the distance of the sleeve window (and/or any marking thereon). For example, the system may confirm that an identifier is present in a target location, corresponding to the inner and/or outer surface of the sleeve window. In variations including an identifier, the identifier may be on an inner and/or outer surface of the sleeve window.

In any of the apparatuses described herein, the intraoral scanner may include one or more electronic agents, in software, firmware, and/or hardware, to assist in authentication and confirming that a sleeve is new and/or is approved for use with the intraoral scanner.

Single Use, Reuse and/or Multiple Use

As described above, in any of the variations described herein the systems and/or sleeves described herein may be configured for single, one-time (e.g., one continuous session) or a limited duration of time use. For example, a system may be configured to identify a sleeve by any of the techniques described herein and may restrict us of the system (e.g., scanning) to a single session and/or a limited duration. The system may include a processor that, upon determining the identity of the sleeve, may limit the use of the identified sleeve to a single continuous session in which the same patient is being scanned. The session may be determined by the scanning of a single patient without a pause in scanning of more than some predetermined amount (e.g., 5 minutes, 10 minutes, 15 minutes, 20 minutes, 30 minutes, 1 hour, etc.). In some variation the session is based on the identity of the patient (e.g., a session ends, requiring a new or newly cleaned sleeve, when a different patient is scanned). The patient identity may be any unique identifier corresponding to a patient, including number, chart number, name, etc.

Any of the sleeves and/or systems described herein may be configured to allow and/or detect cleaning of the sleeve so that it may be reused. Cleaning may include sterilizing. For example, the sleeve may be sterilized by any appropriate technique, including autoclaving, washing, etc. In some variations the identified may be configured to include an identifier that changes after cleaning (and/or sterilizing). For example, the indicator may include a compound that reacts to change (e.g., color, shape, etc.) after exposure to heat within the range of the autoclave. For example, a material such as copper thiosulfate (yellow) changes color (e.g., to a black copper sulfide) under sterilization conditions, typically heat greater than 121 degrees C. Other composition may be barium salts, etc.

Alternatively or additionally the system may mark the sleeve during or after use, e.g., by exposure to light, which may modify a use-sensitive material as described above. In some variations this use-sensitive material may be reset by the cleaning (e.g., sterilizing) process. In some variations the sleeve may be marked (e.g., using a light-sensitive material) to indicate a number of uses. For example, a light-sensitive material may be exposed to a pattern resulting in a marking that may be detected for each use, allowing the number of uses to be indicated and read by the system; after a predetermined number of uses the sleeve may be identified in the local and/or remote system as expired or otherwise prevented from further use.

Window Cover

According to some embodiments, the sleeve includes a protective window cover that covers the window, for example, when the intraoral scanner wand is not being used to scan the patient's dentition. The window cover may protect the window from damage (e.g., scratching) during storage, transport and/or handling of the sleeve. Once the window cover is removed, the window is revealed and ready for use by the scanner. The window cover may also be used as an indicator to signify whether the sleeve has been used or is unused. For example, a sleeve with a window cover may indicate that the sleeve has not been used, while a sleeve without a window cover may indicate that the sleeve has been used. The window cover may be attached to the exterior surface and/or the interior surface of window of the sleeve. In some cases, the window cover is configured to be removed from the sleeve before the sleeve covers the wand. In other cases, the window cover is configured to be removed from the sleeve after sleeve covers the wand.

Figure 8A:
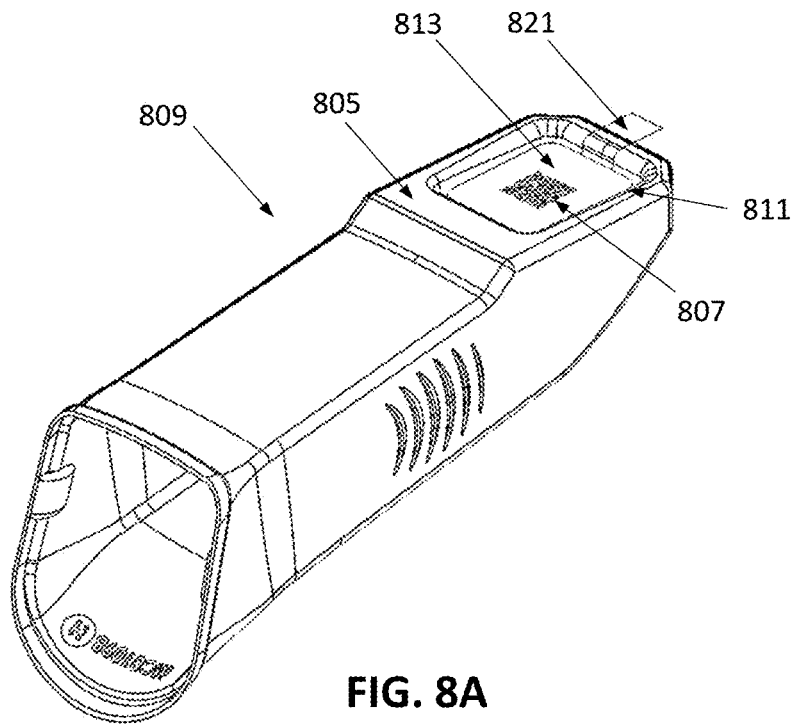
FIGS. 8A-8B illustrate examples of protective sleeves having window covers for protecting the windows and having scannable identifiers.
Figure 8B:
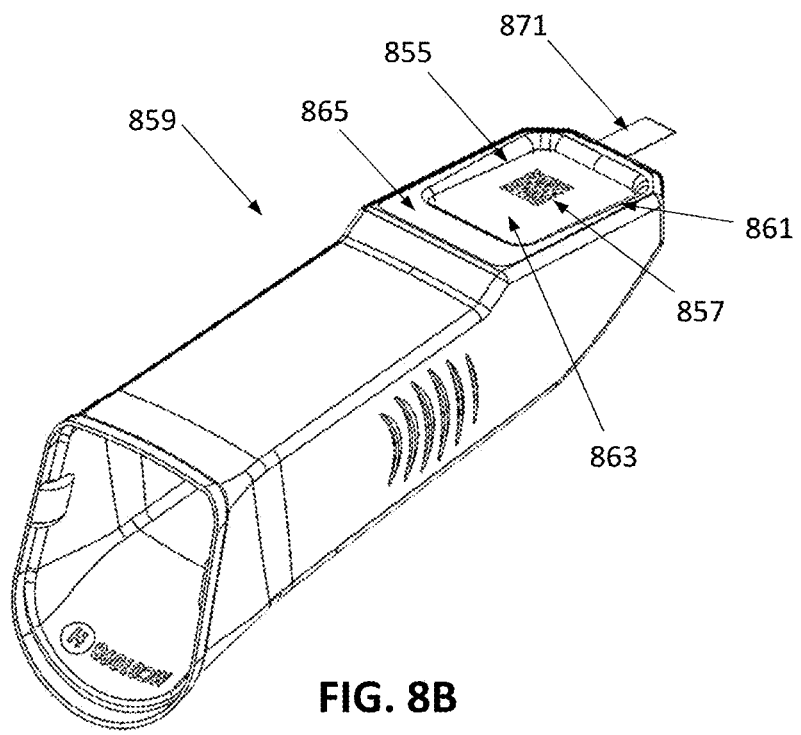

FIGS. 8A-8B illustrate examples of sleeves with window covers. FIG. 8A shows a sleeve 809 that includes a window cover 813 (e.g., adhesive sticker) adhered onto the exterior surface of the window 811. As described herein, the sleeve body can define an opening where the window is supported within. In the embodiment shown, the window is recessed with respect to a frame portion 805 of the sleeve body that frames the window. In some cases, the window cover covers at least a portion of the frame portion 805. In other embodiments, the window cover substantially only covers the window. The sticker may include a tab 821 for easy removal from the window.

FIG. 8B shows a sleeve 859 having similar features as the sleeve of FIG. 8A, except that the window cover 863 is coupled to the frame portion 855 of the sleeve body that frames the window 861. In some embodiments, the window cover is not adhesively coupled to the exterior surface of the window. In some cases, the window cover 863 is frictionally attached (e.g., friction fit) and/or adhesively adhered to the interior edges of the frame portion 855. The window cover may be rigid (e.g., made of a rigid polymer material) to facilitate a friction fit. In other cases, the window cover 863 is compliant (e.g., made of a flexible polymer material) that conforms to the edges of the frame portion 855 of the sleeve body and/or the window. The window cover may include a tab 871 to facilitate removal of the window cover from the sleeve body.

As described herein, the one or more identifiers can be located anywhere on the sleeve, such as within the window area as shown in FIGS. 5A-5C. In some embodiments, the identifier(s) is/are located on a window cover, as shown in the examples of FIGS. 8A and 8B. In particular, identifier 807 is on the window cover 813 of FIG. 8A, and identifier 857 is on the window cover 863 of FIG. 8B. The identifier may be on a separate layer (e.g., sticker) that is adhered onto the window cover with the identifier printed or otherwise disposed thereon. Alternatively or additionally, the identifier may directly applied (e.g., printed on, etched, molded onto, etc.) onto the window cover. In the examples of FIGS. 8A-8B, the identifiers include a QR code. However, the identifier(s) can have be in any form, as described herein. For instance, the identifier(s) may alternatively or additionally include an alphanumeric code, a logo, a symbol, a bar code and/or a mark.

Having the identifier separable from the sleeve body can have several advantages. For example, since the identifier can be removed once it is scanned by the intraoral scanner (wand), the identifier cannot be inadvertently scanned or otherwise interfere with the scanning of the patient's teeth. Thus, there is no need to hide the identifier or make the identifier discrete from the field of view of the scanner. This allows the identifier to be large as needed for easy detection by the wand without interfering with the tooth scanning procedure. The identifier may be disposed on other separable portions of the sleeve other than a window cover, thus providing the advantages described above. For example, the identifier may be on a removable sticker on a different part of the sleeve body (other than the window), which can be separated from the sleeve body once scanned.

Scanner Use Mode

As described herein, the identifier may encode information about a sleeve, such as the sleeve type, use status, batch, serial number, designation and/or other characteristics about the sleeve, which can be scanned and authenticated by the intraoral scanner. In some cases, the information from the identifier may dictate one or more operations of the scanner. As described herein, the intraoral scanning system may be configured to unlock once the identifier is authenticated, thereby giving access to the scanning system. Conversely, the intraoral scanning system may be configured to lock (e.g., turn off) if the identifier is determined not to be authentic. This way, the identifier may block the use of invalid sleeves that would otherwise cause cross-contamination, reduce the scan quality, and/or degrade the quality of the practitioner or patient experience. As described herein, the identifier may be configured for single use to prevent the use of a particular sleeve once it has already been used. The single use model may also prevent the use of duplicate ("fake") identifiers.

In some embodiments, the identifier information is used to set a use mode of the intraoral scanner. A use mode can refer to the various scanner parameters/settings accessible while the scanner is use. The scanner may be designed to operate in more than one use mode, with each use mode allowing access to different scanning parameters/settings. Any of the scanner use modes described herein may be automatically set by the scanning system, for example, once the identifier is authenticated (or unauthenticated) by the scanning system. For example, the scanning system may automatically unlock once the identifier is authenticated, or automatically lock once the identifier is identified as unauthentic. In some cases, the scanning system is configured to provide one or more indicators (e.g., what used mode the scanner is in). For example, the scanning system may provide a message on the display (FIG. 1, 105) and/or an audible alarm.

The use mode can be set based on particular characteristics of the sleeve. For example, some sleeve types may be designed for use with certain types of scanning procedures but not others. The use mode can be set based on the compatibility of the sleeve with the scanner. For example, some sleeves may only be compatible to operate with certain types/models of scanners and not others. In some cases, different used modes allow the scanner to operate in one or more different scanning modes (e.g., optical wavelengths, fluorescent wavelengths, and/or near infrared imaging (NIRI) wavelengths).

The use mode can be set based on the type of sleeve. For example, the identifier information may define whether the user is allowed to interrupt a scan (e.g., to remove the sleeve for cleaning) and to complete the scanning process using the same sleeve. This kind of permission may be useful for removable sleeves that are designed to be cleaned between scanning procedures rather than being disposed of.

In some cases, the use mode is associated with the customer using the intraoral scanner. For example, different customers may desire access to different modes/levels of scanning operations. Thus, the identifier on the sleeve can convey such information to the scanner and the scanning operating parameters are set accordingly. This scheme can allow for a pay per scan implementation or other customized use setting based on a pre-arranged agreement, thereby providing more flexibility for customers.

Methods of Use

Figure 7:
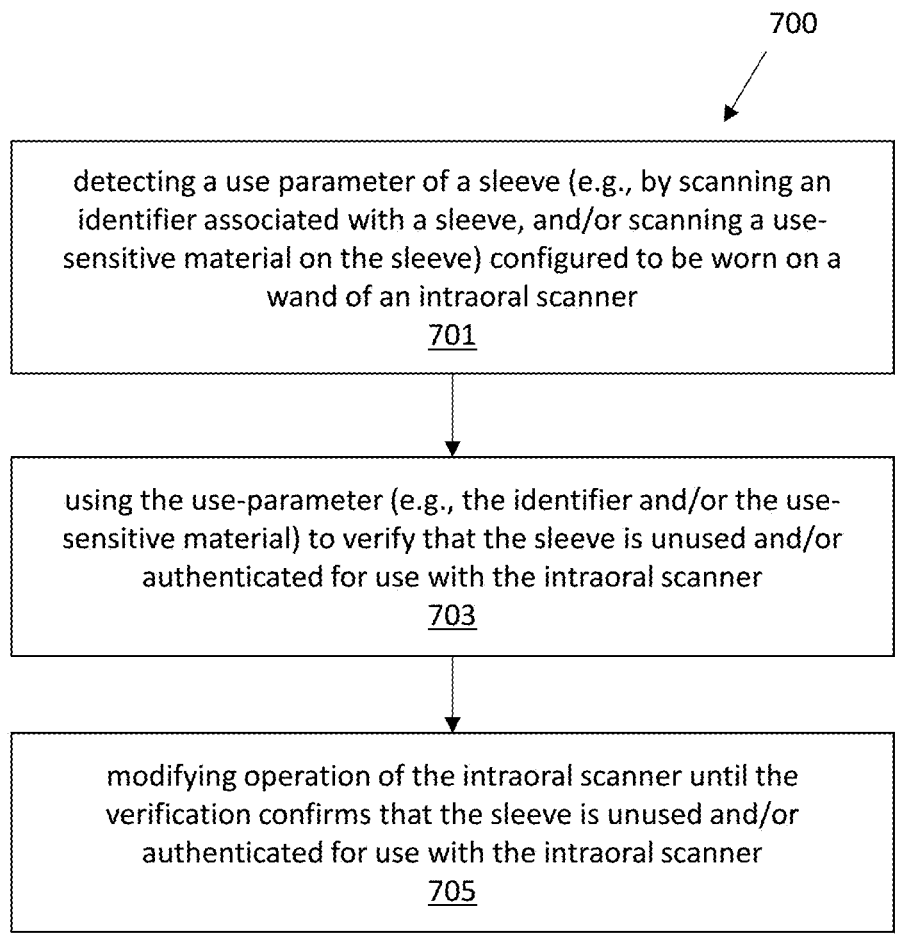
FIG. 7 illustrates one example of a method of operating an intraoral scanner including detecting a use parameter for a sleeve (e.g., directly or through detection of an identifier associated with the sleeve) and modifying the activity of the intraoral scanner based on the use parameter.

FIG. 7 illustrates one example of a method 700 of operating an intraoral scanner by determining a user parameter of a sleeve and adjusting the operation of the intraoral scanner accordingly. For example, as illustrated in FIG. 7, the method may include detecting a user parameter with the intraoral scanner 701. The use parameter may be an identifier that is associated with the sleeve, including uniquely associated with the sleeve. In some variations the use parameter is a directly detected use-sensitive material, such as a composition that is modified in response to use of the sleeve by an intraoral scanner. The use parameter (e.g., identifier) for the sleeve may be detect as illustrated and described above, typically by scanning or otherwise receiving information associated with the sleeve using the wand of the intraoral scanner. For example, the wand may optically detect (image) the surface(s) of the sleeve window. This step may be performed before, during or after attaching the sleeve to the wand.

The use parameter may then be used to verify that the sleeve is unused and/or that the sleeve is authenticated for use with the intraoral scanner 703. This may include using a processor of the intraoral scanner and/or a remote processor/database in communication with the intraoral scanner to confirm the identity of the sleeve and any tracking information about it (used, expiration, category, lot, zone of approved use, etc.). In some variations the use parameter may include information about the modification to the intraoral scanner for use specific to the sleeve.

Thus, the method may include modifying the operation of the intraoral scanner until the verification confirms that the sleeve is unused and/or authenticated for use with the intraoral scanner 705. The intraoral scanner may be modified by suspending operation (scanning) of a patient until a new sleeve is detected. One or more user interfaces may be used as part of any of these steps, including providing user instructions for use.

Figure 10:
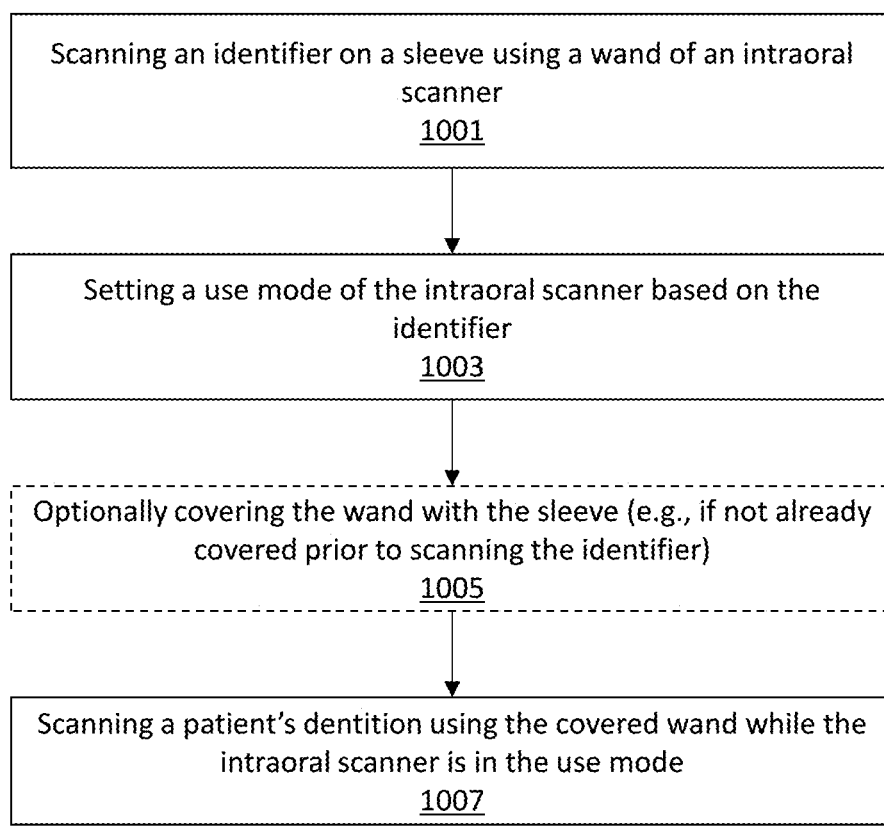
FIG. 10 illustrates another example of a method of operating an intraoral scanner including setting a use mode of the scanner based on information from a scanned identifier on a sleeve.

FIG. 10 illustrates another example of a method 1000 of operating an intraoral scanner. An identifier on a removable protective sleeve is scanned using a wand of the intraoral scanner 1001. In some variations the sleeve is scanned after being applied onto the wand. In some variations the sleeve is scanned prior to being applied (e.g., attached, worn over, etc.) the wand. This identifier can include encoded information related to the sleeve, such as the status of the sleeve (e.g., used or unused), model number (e.g., indicating compatible scanners), batch number (e.g., indicating manufacturing process), customer number (e.g., indicating a purchasing history) and/or other identifying information. In some embodiments, the identifier is on, or part of, a removable portion of the sleeve that can be removed prior to performing a scanning operation on the patient's dentition. For example, the identifier may be on, or part of, a window cover that covers and protects the sleeve window prior to use.

The sleeve identifier can be used to set a used mode of the intraoral scanner 1003. For example, the identifier can include authentication information indicating that the sleeve is suitable for use with the scanner, thereby unlocking one or more scanning operation modes of the scanner. If the identifier may include sleeve status information (e.g., used or unused), this information can also be used to lock or unlock one or more scanning operation modes of the scanner. If the identifier includes information related to compatibility with certain types or models of scanners, this information can be used to lock operation of the scanner except for use with those sleeves determined to be compatible.

In some variations, once the identifier of the sleeve is scanned, the wand of the intraoral scanner can be covered with the sleeve 1005 in order to protect the patient from cross-contamination. Note that in some variations the sleeve may be scanned after it is placed on the wand (e.g., through the window), as described herein. If the identifier is on a removable portion of the sleeve, the identifier can be removed from the sleeve. This can be done prior to the sleeve being placed on the wand of the scanner, or after the sleeve is place on the wand of the scanner. In embodiments where the identifier is on (or part of) a window cover, the window cover (with the identifier) can be removed from the window to reveal the sleeve window. The patent's dentition can then be scanned using the sleeve-covered wand 1007.

EXAMPLES

Figure 11A:
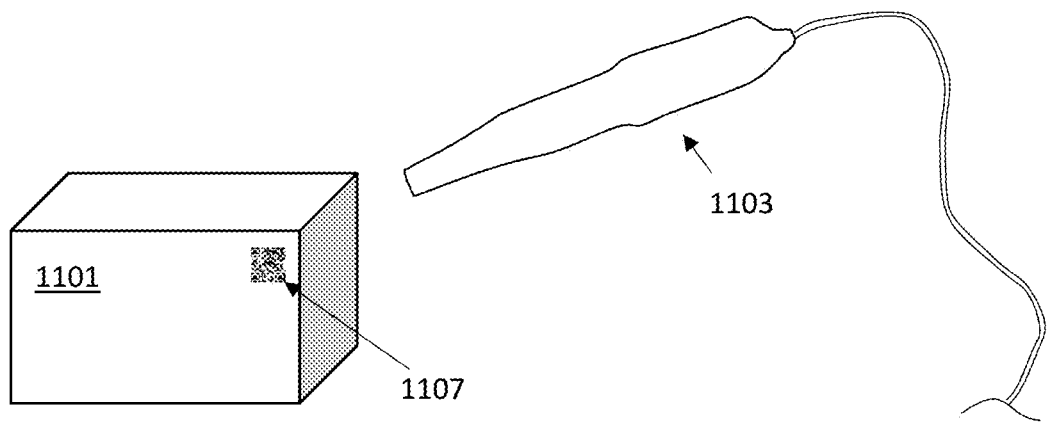
FIG. 11A is one example illustrating the operation of a system for authenticating a sleeve for an intraoral scanner, in which a plurality of sleeves are packaged in a container holding multiple sleeves; the container may be scanned by the intraoral scanner prior to coupling one of the sleeve to the intraoral scanner.

In some variations authentication includes authentication of a sleeve based on packaging associated with the sleeve. For example, FIG. 11A illustrates one example of a method of authenticating a sleeve for use with an intraoral scanner 1103 using the intraoral scanner itself, including a wand or hand-held portion of the intraoral scanner, to scan an identifier (e.g., code, such as a QR code, bar code, etc.) 1107 on the packaging enclosing one or more sleeves. In FIG. 11A, the box 1101 includes a plurality of, e.g., n, sleeves. In some variations the QR code may be scanned by the intraoral scanner, which may permit the intraoral scanner to operate for n scans (e.g., one scan per sleeve). As mentioned, in in some variations the code may enable oral cavity scanning by the intraoral scanner, and may therefore disable or suspend intraoral scanning until authentication by a valid code.

In some variations the identifier 1107 may also or alternatively indicate information about the sleeve(s) within the box, such as material properties, optical properties, expiration date, country verification code, etc. Scanning the identifier 1107 may modify the operation of the intraoral scanner by enabling/disabling operation of the intraoral scanner, modifying the optics of the intraoral scanner (e.g., intensity, wavelength, scan rate, etc.), and/or displaying one or more messages to the user (e.g., dental professional). For example, the intraoral scanner optics may be matched to the optics of the sleeve window based on the information from the identifier. In some variations the authentication identifier (e.g., code) may be used to verity that the sleeve is compatible with the region (e.g., based on region). A display may inform the user that the sleeve is authentic and/or compatible with this region or that is not compatible and/or not authentic. In some variations the intraoral scanner may determine that, based on the identifier, the sleeve is appropriate for the country or other jurisdiction in which the scanner is being operated; in some locations regulations regarding the use of the sleeve and intraoral scanner may be different, and the system may indicate that indicate the type of sleeve is appropriate or not appropriate for the specific location in which the intraoral scanner is located. For example, some regions may require that the intraoral scanner be used with a sleeve that extends longer than 14 inches, whereas other regions may allow sleeves that extend only to 12 inches. In some variations the sleeve must be made of a particular material, etc. The authentication identifier may include this information within the identifier, or it may refer to a reference (e.g., look up table, database, either remote or local to the intraoral scanner) to determine compatibility. The system may include an output indicating one or more messages and/or may lock out the user from using sleeves that are indicated as not appropriate for a particular region or device, or may simply provide a warning.

Figure 11B:
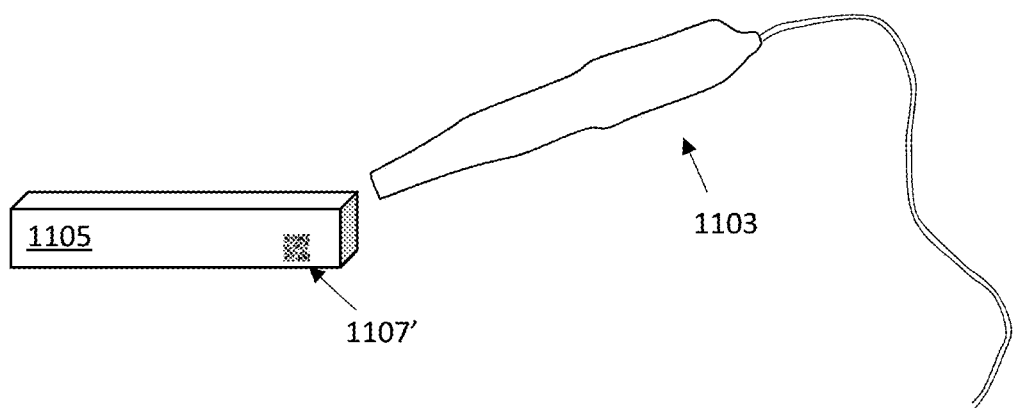
FIG. 11B is another example illustrating the operation of a system for authenticating a sleeve for an intraoral scanner in which a single sleeve is contained with a container.

FIG. 11B shows another example of a system and method of operating an intraoral scanner with authentication as described herein. In FIG. 11B, the intraoral scanner 1103 may be used to scan an identifier 1107' on the outside (or in some variations the inside) of a container 1105, e.g., packaging, holding a single sleeve. As mentioned, the identifier may be one or more of: an alphanumeric code, a logo, a symbol, a QR code, a bar code, etc. Alternatively or additionally, an identifier (e.g., authentication code) may be packaged with the sleeve, e.g., on an insert, paper or other accompanying material.

Figure 12A:
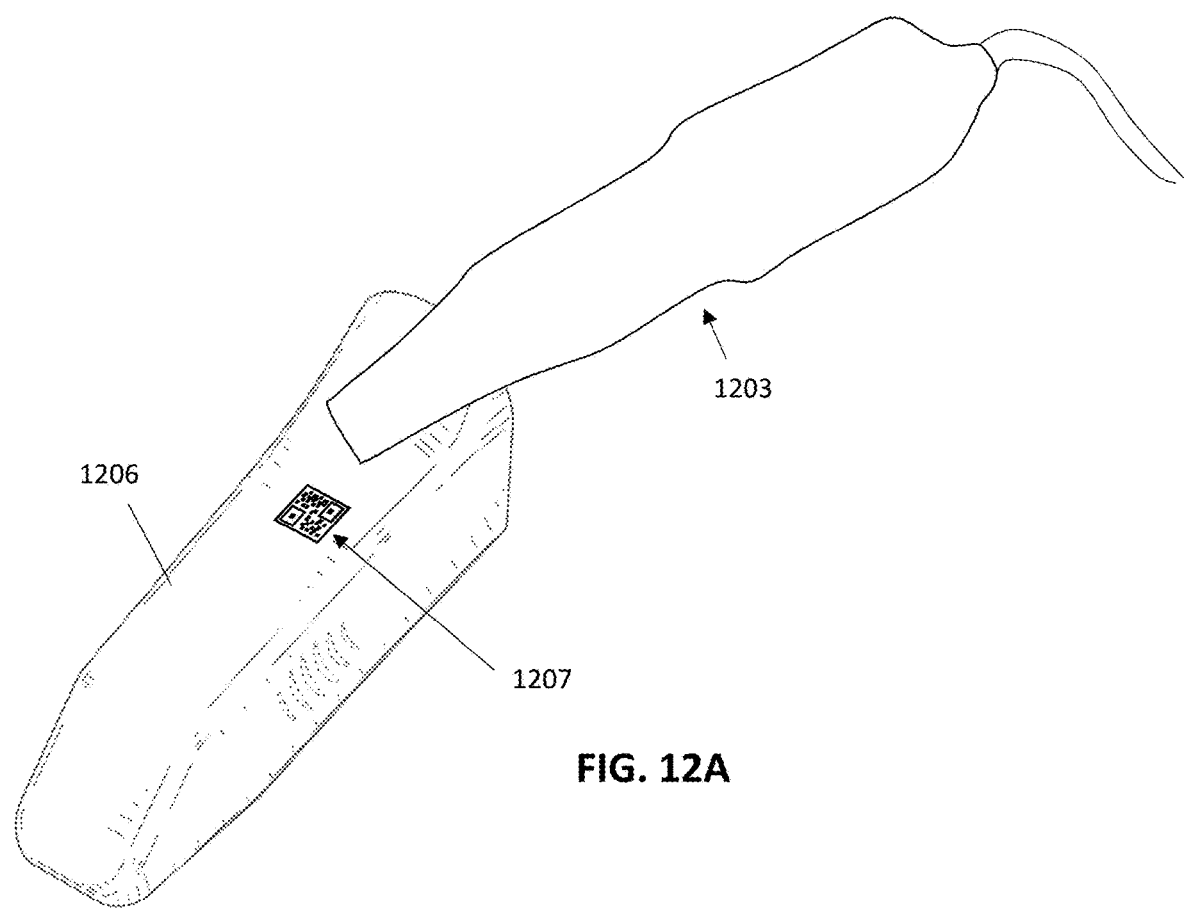
FIG. 12A illustrates a method of authenticating a sleeve by scanning, using an intraoral scanner, a code (e.g., a QR code is shown) on an outside of the sleeve prior to coupling the sleeve with the intraoral scanner.

As mentioned above, in some variations one or more authentication identifiers may be included on the sleeve itself. FIG. 12A shows an example in which the identifier 1207 (shown in this example as a QR code) is on the outside of the sleeve and is scanned by the hand-held wand of the intraoral scanner 1203. After scanning, the intraoral scanner wand may be placed into the sleeve 1206 so that the two engage and the optics of the intraoral scanner line up with the window (not visible in FIG. 12A) of the sleeve.

Figure 12B:
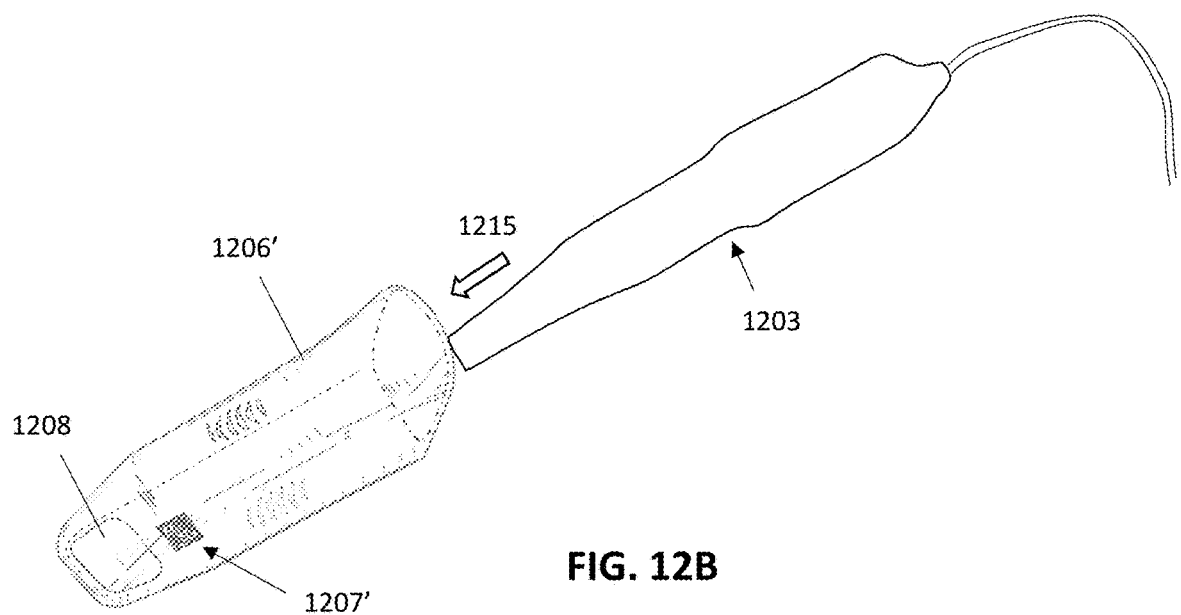
FIG. 12B illustrates a method of authenticating a sleeve by scanning, using an intraoral scanner, a code on an inside of the sleeve as the scanner is coupled with the sleeve.

Alternatively or additionally one or more identifiers may be included in the inside of the sleeve 1206', as shown in FIG. 12B. In FIG. 12B, the wand of the intraoral scanner 1203 is slid into the sleeve 1206', as shown by the arrow 1215, so that the sleeve may engage with the intraoral scanner. In this example, the identifier is adjacent to the window 1208 region on the inside of the sleeve so that the intraoral scanner scans it as it is inserted into the sleeve. The intraoral scanning system may automatically identify the identifier (e.g., code 1207') and the identifier may then modify the activity of the intraoral scanner as described herein.

For example, in some variations of the methods and apparatuses (e.g., systems) described herein, the intraoral scanner may be configured sot that it is turned on to allow scanning, and in particular scanning of the identifier on a sleeve or sleeve packaging, in a first mode of operation. This mode of operation may be timed (e.g., the intraoral scanner may allow scanning for a period of time that is sufficient to scan the identifier, patient face, user face, chart, etc.) but may not be on long enough to scan the dentition. This first mode (e.g., the authentication mode or sleeve authentication mode) may be limited to scanning in a manner that does not permit (pending an override by the user) of the teeth. This may prevent operation of the intraoral scanner in a manner that is contrary to safety or public policy (e.g., without the protection of a sleeve. Once the system detects a sleeve and authenticates the sleeve as described herein, the intraoral scanning system may switch to a second (intraoral scanning, or post-authentication) mode in which the patient's oral cavity may be scanned, displayed, and/or saved as part of a patient file.

The authentication step, in which the authentication code is identified and reviewed either locally and/or remotely (if communications, such as internet communications, are available) may modify the operation of the intraoral scanner, including allowing a transition between the authentication mode of operation and the intraoral scanning mode, and/or enabling certain functions of the intraoral scanner or processing of the scan data.

In some variations the sleeve identifier may be tied to a processing code that indicates to the intraoral scanning system how the patient scan should be processed. For example, in some variations sleeves may be marked as part of the identifier (e.g., code, etc.) for use in generating a particular orthodontic and/or dental model or program, such as for generating a series of dental aligners to move teeth. The identifier (e.g., code) on the sleeve may cause the intraoral scanner to process the intraoral scan either during scanning (e.g., confirming that the scan data is appropriate for modeling the patient's dental arch for the procedure(s) indicated on the sleeve identifier, and/or for post-scan processing, e.g., transmitting the scan for generating a dental treatment plan as indicated by the sleeve identifier. Identifier (e.g., codes) on sleeves may therefore include promotional codes (including pricing and discount information). In some variations the identifier may cause the intraoral scanning system to generate user interfaces that are specific to one or more identified procedures or the like.

In some variations the intraoral scanning systems described herein may be configured to identify when the sleeve is being applied and/or removed. For example, in the variation shown in FIG. 12B, if the intraoral scanner is in a scanning mode and the intraoral scanner detects the identifier (e.g., QR code 1207') the system may infer that the sleeve is being removed. In this case the intraoral scanner may switch into a post-scanning mode, and/or back into an authentication mode.

Figure 12C:
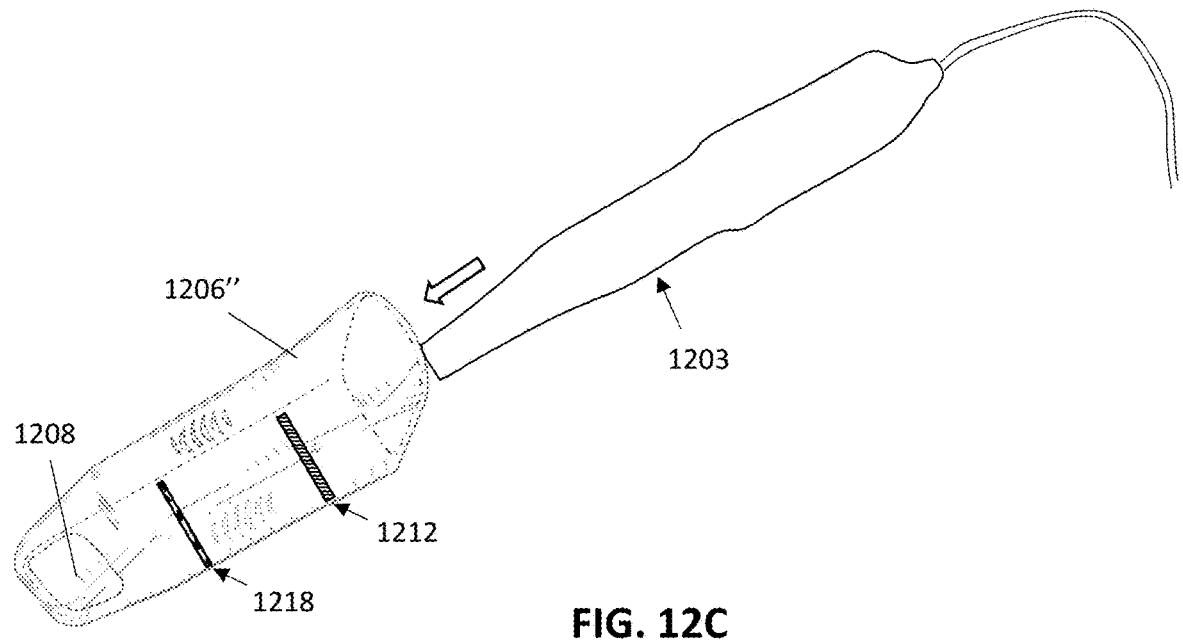
FIG. 12C illustrates another example of a method of authenticating a sleeve by receiving orientation information as the scanner is inserted into the sleeve; this information may indicate that the sleeve is being applied or removed, or other use information about the sleeve.

FIG. 12C shows another example of a sleeve 1206" in which a pair of identifiers 1212, 1218 are included within the inside of the sleeve. In this example, the scanner 1203 may sequentially scan these identifiers within a reasonable time window (e.g., a few seconds, a minute, etc.) and the order in which the two identifiers are scanned may indicate if the sleeve is being placed onto the intraoral scanner or being taken off of the intraoral scanner. For example, if the intraoral scanner passes the first identifier 1212 before the second identifier 1218, then it is likely that the sleeve is being placed onto the intraoral scanner 1203. The first and second identifiers are therefore typically different and may be different colors, patterns, alphanumerics, logos, etc. In some variations the first and/or second identifiers may also encode information as described herein. In any of these variations, the system (e.g., the intraoral scanner) may count the number of times a sleeve is placed on/taken off.

In variations in which the sleeve may be reused (e.g., with the same patient), the intraoral scanner may identify the number of uses and/or may limit the number of uses. In some variations the system may prompt the user to confirm that the sleeve has been sterilized or cleaned; the intraoral scanner may uniquely identify that the sleeve has been used before (either on the same intraoral scanner or a different intraoral scanner). In some variations the system may confirm, based on the identifier and patient-specific identifying information, either manually or automatically entered about the patient, including the patient name or other unique identifier.

As mentioned, any of the apparatuses (e.g., intraoral scanning systems) described herein may be configured to confirm that a sleeve, or in some cases a sleeve of the appropriate type, model, batch, etc., or a "new" (unused) sleeve, is being used. In some variations the apparatus may be configured to prevent operation in the oral cavity scanning mode if there is no sleeve on, or if the sleeve is not appropriate.

Figure 13:
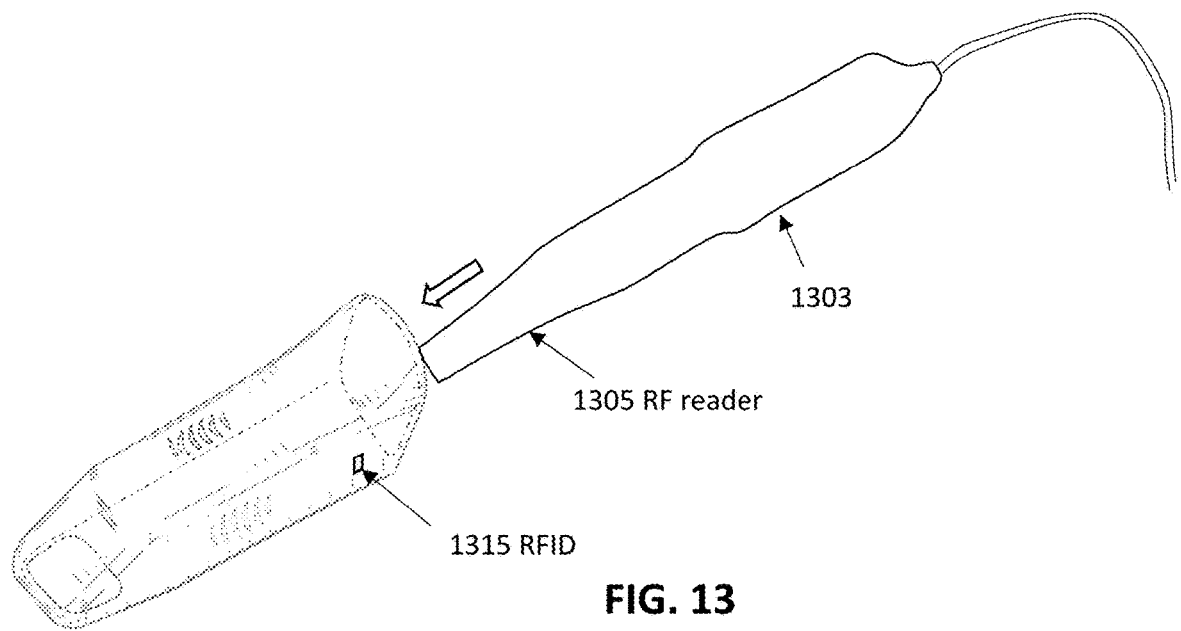
FIG. 13 illustrates another example of a method of authenticating a sleeve using a marker in or on the sleeve that is detected by a sensor on the intraoral scanner.

The examples provided above (e.g., in FIGS. 11A-12C) are optical authentication systems and methods, in which the identifier is optically scanned, preferably the existing scanning components of the intraoral scanner that will be used to scan the teeth and other parts of the intraoral cavity. Is some variations one or more non-optical identifiers (and detectors) may be used, such as radio frequency (RF) tags (e.g., RFIDs), ultrasound, nearfield, Bluetooth, etc. These authentication identifiers and/or detectors may be present on sleeve and/or wand. For example, FIG. 13 shows a variation in which an RFID tag 1315 is included as part of the sleeve (e.g., on an inside or outside of the sleeve) and the intraoral scanner (e.g., wand 1303) includes an RFID reader 1305, as shown. This may be used in addition or optical scanning.

As described above, in some variations you may run the intraoral scanner prior to engaging the sleeve, in order to detect and authenticate the sleeve by scanning the identifier (e.g., code). This scanner may therefore be operated in a pre-scanning (e.g., authentication) mode until authentication is complete. In some variation the scanner may be attached to the sleeve without scanning first. Once the sleeve is attached over the intraoral scanner may be operated to detect the sleeve. For example in variation in which an identifier is present on the window of the sleeve (or as a removable decal over the window) the intraoral scanner may immediately detect and react to the identifier. In some variations, such as when the identifier is present on the inside or outside of the sleeve the intraoral scanner may be removed from the sleeve, the identifier scanned, and the sleeve reapplied. In some variations, as when the identifier is partially within the sleeve, the sleeve may be partially removed, and the identifier scanned as it is partially removed; the intraoral scanner apparatus may indicate successful authentication (or at least successful identification of the identifier), and the sleeve immediately reapplied.

In some variations the identifier may be used to limit the time that the same sleeve may be used with an intraoral scanner. For example the identifier may uniquely identify the sleeve and the intraoral scanner system may time how long the sleeve is used for before it is removed. Once removed the identifier associated with the sleeve may be set (e.g., within a local and/or remove database accessible by the intraoral scanner) indicating that the sleeve has been used (or the number of times that it's been used). Further, as mentioned, the intraoral scanner apparatus may "time out" a sleeve after it has been used for a predetermined, or in some cases selectable, time period. In some variations the intraoral scanner may be configured to prevent the same sleeve from being used with a different patient. For example, if the user changes to another patient record, the intraoral scanner apparatus may require a new sleeve based on the authentication identifier and/or a previously used sleeve that was previously used with that patient. In some variations, as mentioned above, the apparatus may detect that the sleeve has been sterilized and/or may prompt the user to confirm that the same sleeve, based on the identifier, has been sterilized.

The information that may be encoded and/or associated with the identifier (e.g., identification code), as mentioned above, may include a unique identifier (number, alphanumeric, etc.) that may be specific to the sleeve, and/or specific to a type, class, lot, batch, etc. of sleeve(s). In some variations, as mentioned above, the sleeve identifier may include or be associated with a region code. In some variations the identifier includes information or is associated with information regarding the lot number, an expiration date, a region code, a practice code, a promotional/marketing code, a procedure code (e.g., aligner sleeve, infrared sleeve, palatal expander sleeve, caries detection sleeve, etc.), a recall code, etc.

As mentioned the code may itself include/encode any of the information described above, or it may be associated either locally (e.g., in a local memory on an intraoral scanner) and/or remotely (e.g., on database that one or more intraoral scanners connects to continuously and/or periodically). An identifier may be "associated" with information in a number of ways. For example, the identifier or a portion of the identifier may be used as an index to a look-up table or database containing information about one or more of these classes of information that is linked to the identifier.

Figure 14:
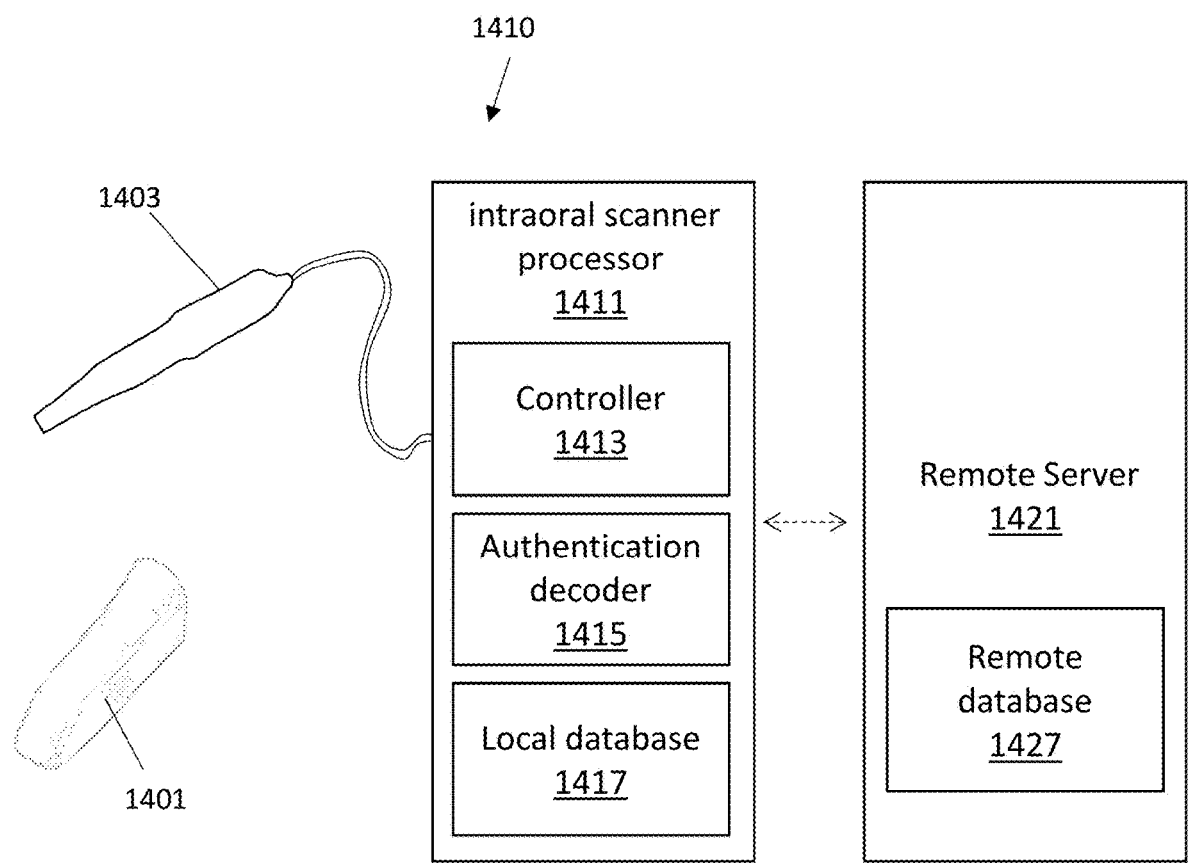
FIG. 14 schematically illustrates one example of an intraoral scanning system configured to include and implement sleeve authentication as described herein.

For example, FIG. 14 shows one example of an intraoral scanning system 1410 as described herein, including a hand-held intraoral scanning wand 1403 and an intraoral scanning processor 1411. In FIG. 14 the two are shown as separate and connected by a cord; alternatively the intraoral scanner processor 1411 may be coupled wirelessly to the wand 1403 and/or may be integrated completely or partially into the wand (not shown). The intraoral scanner processor 1411 may include a controller (e.g., control circuitry) 1413, an authentication decoder 1415, and a local datastore or database 1417. The intraoral scanner processor may include a number of other modules, including optical control (imaging) modules, scanning control modules, inputs (e.g., user inputs, buttons, keyboards, etc.) and outputs (e.g., displays, LEDs, audio outputs, etc.), not shown in this figure. In general, one or more of these apparatuses 1410 may be in continuous or period (hourly, daily, weekly, monthly, etc.) and/or intermittent (e.g., on demand, irregular, etc.) communication with a remote server 1421, including a remote database 1427. The remote server may provide updates to the local database 1417 and/or authentication decoder 1415 and/or controller 1413. For example the intraoral scanner may pass patient scan data on to the remoter server for further processing.

In use, the intraoral scanner may authenticate a sleeve 1401 as described above, including using the wand of the intraoral scanner 1403 with imaging optics for imaging the intraoral cavity, and apply these imaging optics to scanning the identifier on the sleeve 1401. As mentioned, the intraoral scanner may be held in a pre-authenticated mode prior to authentication, which may limit the functioning of the intraoral scanner 1410 until authenticated. Once the intraoral scanner (e.g., wand 1403) scans the identifier on or associated with a sleeve (or group of sleeves) the identifier may be processed by the authentication decoder 1415 to parse and/or interpret/apply the identifier and authenticate the sleeve. An authentication decoder may be module, and may include hardware, software and/or firmware for parsing the identifier. The authentication decoder 1415 may use the imaging data from the scan(s) being taken (typically at a high rate) and process the images (or groups of images) and extract from the image(s) the authentication identifier. This identifier may then be interpreted by the authentication decoder, including by using the local database 1417 to look up information (and in some variations control instructions) associated with the identifier. In some variations the authentication decoder may pass information and/or instructions based on the decoded identifier on to the controller for controlling operation of the intraoral scanner, including authenticating the sleeve and entering into an intraoral scanning mode, locking the intraoral scanner to prevent scanning until authentication, displaying user information, instructions and/or user interface(s), modifying the operation of the optics, light sources, scanning control, oral cavity reconstructions, etc., based on the identifier.

The architecture shown in FIG. 14 is one variation of an intraoral system. Other variations may be used. For example, in some variations authentication and control is limited to just local operation (e.g., the authentication decoder and/or local database may not communicate with a remote server). Alternatively in some variations, the system is continuously linked to a remote server (or semi-remote server, which may communicate locally with multiple intraoral scanners, e.g., in a clinic or office); in this configuration the individual intraoral scanner may not include an authentication decoder and/or local database, or may include only a simplified authentication decoder and/or local database, and instead may transfer more rigorous decoding of the identifier to the remote or semi-remote servers. In some variations the intraoral scanner does not include a database (e.g., look-up database). The intraoral scanner architecture shown in FIG. 14 may be particularly beneficial in situations.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A sleeve for an intraoral scanner, the sleeve comprising:
   a sleeve body configured to fit onto the intraoral scanner, the sleeve body including a window formed of an optically transparent material, wherein the window is configured to align with a field of view of the intraoral scanner when the sleeve body is attached to the intraoral scanner; and
   a removable window cover attached to the window and being removable from the window for transmission of light from the intraoral scanner, the window cover including an identifier that is scannable by the intraoral scanner when the window cover is attached to the window and that identifies one or more characteristics of the sleeve.

2. The sleeve of claim 1, wherein the identifier is scannable by the intraoral scanner prior to placing the sleeve body on the intraoral scanner.

3. The sleeve of claim 1, wherein the identifier is disposed on a sticker that is adhesively coupled to the window cover or the window.

4. The sleeve of claim 1, wherein the removable window cover is frictionally coupled to a frame portion of the sleeve body.

5. The sleeve of claim 4, wherein the removable window cover is made of a rigid polymer material to facilitate a friction fit to the frame portion.

6. The sleeve of claim 1, wherein the removable window cover is configured to protect the window during storage or handling of the sleeve.

7. The sleeve of claim 1, wherein the removable window cover is configured to be removed from the sleeve before the sleeve covers the intraoral scanner.

8. The sleeve of claim 1, wherein the removable window cover is configured to be removed from the sleeve after sleeve covers the intraoral scanner.

9. The sleeve of claim 1, wherein the removable window cover comprises a tab configured to facilitate removal of the window cover from the sleeve body.

10. The sleeve of claim 1, wherein the identifier comprises a QR code.

11. The sleeve of claim 1, wherein the identifier comprises one or more of: an alphanumeric code, a logo, a symbol, a bar code and/or a mark.

12. An intraoral scanning system, the system comprising:
    an intraoral scanner; and
    a sleeve configured to fit onto the intraoral scanner, the sleeve comprising:
      a sleeve body including a window formed of an optically transparent material, wherein the window is configured to align with a field of view of the intraoral scanner when the sleeve body is attached to the intraoral scanner; and
      a removable window cover attached to the window and being removable from the window for transmission of light from the intraoral scanner, the window cover including an identifier that is scannable by the intraoral scanner when the window cover is attached to the window and that identifies one or more characteristics of the sleeve,
    wherein the intraoral scanner is configured to verify that the identifier is authenticated for the intraoral scanner by scanning the identifier, and to modify operation of the intraoral scanner based on the identifier.

13. The system of claim 12, wherein the identifier is located on the window and impinges into a field of view of the intraoral scanner when the sleeve is worn on the intraoral scanner.

14. The system of claim 12, wherein the intraoral scanner is configured to modify one or more operating parameters of the intraoral scanner once the identifier is authenticated.

15. The system of claim 12, wherein the identifier is located on the window without impinging substantially into a field of view of the intraoral scanner when the sleeve is worn on the intraoral scanner.

16. An intraoral scanning scanner system, the system comprising:
- an intraoral scanner; and
- a sleeve configured to fit onto the intraoral scanner, the sleeve comprising:
    - a sleeve body including a window formed of an optically transparent material, wherein the window is configured to align with a field of view of the intraoral scanner when the sleeve body is attached to the intraoral scanner; and
    - a removable window cover attached to the window and being removable from the window for transmission of light from the intraoral scanner, the window cover including an identifier that is scannable by the intraoral scanner when the window cover is attached to the window and that identifies one or more characteristics of the sleeve, wherein the intraoral scanner is configured to verify that the identifier is authenticated for the intraoral scanner by scanning the identifier, and to automatically set a particular use mode of the intraoral scanner based on the scanned identifier, wherein the particular use mode dictates one or more scanning parameters of the intraoral scanner and is one of a number of different use modes of the intraoral scanner.

17. The system of claim 16, wherein the identifier is located on the window and impinges into a field of view of the intraoral scanner when the sleeve is worn on the intraoral scanner.

18. The system of claim 16, wherein the identifier is located on the window without impinging substantially into a field of view of the intraoral scanner when the sleeve is worn on the intraoral scanner.

* * * * *